US007265260B2

(12) United States Patent
Bol et al.

(10) Patent No.: US 7,265,260 B2
(45) Date of Patent: Sep. 4, 2007

(54) TRANSGENIC NON-HUMAN MAMMALS EXPRESSING CONSTITUTIVELY ACTIVATED TYROSINE KINASE RECEPTORS

(75) Inventors: David K. Bol, Gaithersburg, MD (US); Joan M. Carboni, Yardley, PA (US); Ronald B. Rowley, Guilford, CT (US); Tai W. Wong, Belle Meade, NJ (US); Francis Y. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 477 days.

(21) Appl. No.: 10/378,393

(22) Filed: Mar. 3, 2003

(65) Prior Publication Data

US 2003/0182668 A1    Sep. 25, 2003

Related U.S. Application Data

(60) Provisional application No. 60/360,889, filed on Mar. 1, 2002.

(51) Int. Cl.
*A01K 67/027* (2006.01)
*A01K 67/00* (2006.01)
*C07H 21/04* (2006.01)

(52) U.S. Cl. .............................. 800/18; 800/13; 800/14; 536/23.5; 536/24.1

(58) Field of Classification Search ................. 800/13, 800/14, 21, 25, 18; 536/23.5, 24.1
See application file for complete search history.

(56) References Cited

U.S. PATENT DOCUMENTS

| 4,873,191 | A | 10/1989 | Wagner et al. |
| 5,686,281 | A | 11/1997 | Roberts |
| 5,712,149 | A | 1/1998 | Roberts |
| 5,741,899 | A | 4/1998 | Capon et al. |
| 5,837,544 | A | 11/1998 | Capon et al. |
| 6,077,947 | A | 6/2000 | Capon et al. |

FOREIGN PATENT DOCUMENTS

| WO | WO99/57268 | 11/1999 |
| WO | WO 02/079192 | 10/2002 |

OTHER PUBLICATIONS

Kappel et al., 1992, Current Opinion in Biotechnology, vol. 3, p. 548-553.*
Wall, R. J., 1996, Theriogenology, vol. 45, p. 45-68.*
Strojek et al., 1988, Genetic Engineering: Principles and Methods, vol. 10, pp. 221-246.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
Mercier et al., 1997, "The modification of milk protein composition through transgenesis: progress and problems," In: Transgenic Animals: Generation and use, Ed. Houdebine LM, Harwood Academic Publishers, The Netherlands pp: 473-482.*
Kiguchi et al., 2000, Oncogene, vol. 19, p. 4243-4254.*
Jeffers et al., 1998, PNAS, vol. 95, pp. 14417-14422.*
Capecchi, Mario, Cell, vol. 22, pp. 479-488 (1980).
Gordon et al., Proc. Natl. Acad. Sci. USA, vol. 77, No. 12, pp. 7380-7384 (1980).
Wagner et al., Proc. Natl. Acad. Sci. USA, vol. 78, No.10, pp. 6376-6380 (1981).
Baserga, Renato, Cancer Research, vol. 55, pp. 249-252 (1995).
Kato, et al., The Journal of Biological Chemistry, vol. 268, No. 4, pp. 2655-2661 (1993).
Gronborg, et al., The Journal of Biological Chemistry, vol. 268, No. 31, pp. 23435-23440 (1993).
Ottensmeyer et al., Biochemistry, vol. 39, No. 40, pp. 12103-12112 (2000).
Baer et al., Biochemistry, vol. 40, pp. 14268-14278 (2001).
Bol et al., Oncogene, vol. 14, pp. 1725-1734 (1997).
DiGiovanni et al., Cancer Research, vol. 60, pp. 1561-1570 (2000).
Zong et al., The EMBO Journal, vol. 15, No. 17, pp. 4515-4525 (1996).
Sukhatme et al., Cell, vol. 40, pp. 591-597 (1985).
Morrione et al., Journal of Virology, vol. 69, No. 9, pp. 5300-5303 (1995).
Muller et al., Cell, vol. 54, pp. 105-115 (1988).
Fiebig et al., Contrib. Oncol. Basel. Karger, vol. 42, pp. 321-351 (1992).
Omer et al., Cancer Research, vol. 60, pp. 2680-2688 (2000).
Park et al., Proc. Natl. Acad. Sci. USA, vol. 84, pp. 6379-6383 (1987).
Tennagels et al., Biochemical & Biophysical Research Communications, vol. 260, pp. 724-728 (1999).
Al-Hasani et al., FEBS Letters, vol. 400, pp. 65-70 (1997).
Ullrich et al., The EMBO Journal, vol. 5, No. 10, pp. 2503-2512 (1986).
DiGiovanni et al., PNAS, vol. 97, No. 7, pp. 3455-3460 (2000).
Wilker et al., Molecular Carcinogenesis vol. 25, pp. 122-131 (1999).
Schwaller et al., The EMBO Journal, vol. 17, No. 18, pp. 5321-5333 (1998).
Carron et al., Blood, vol. 95, No. 12, pp. 3891-3899 (2000).
Andrecheck, E.R. et al., Breast Cancer Res., vol. 2, pp. 211-216 (2000).
Amicone, L. et al., The EMBO Journal, vol. 16, No. 3, pp. 495-503 (1997).
Augustine, K.A. et al., J. Cell Physiol., vol. 181, pp. 433-447 (1999).

(Continued)

*Primary Examiner*—Shin-Lin Chen
(74) *Attorney, Agent, or Firm*—Paul D. Golian

(57) ABSTRACT

A transgenic non-human mammal whose germ cells and somatic cells contain a constructively activated tyrosine kinase receptor introduced into the mammal, or an ancestor of the mammal, at an embryonic stage. The transgenic non-human mammals can be used as ligand-independent in vivo models for the identification and development of selective tyrosine kinase modulators for the treatment of cancer.

11 Claims, 11 Drawing Sheets

OTHER PUBLICATIONS

De Graaffe E. et al., Genes and Development, vol. 15, pp. 2433-2444 (2001).
Egeblad, M. et al., Int. J. Cancer, vol. 94, pp. 185-191 (2001).
Gestblom C. et al., Am. J. Pathol., vol. 155, No. 6, pp. 2167-21279 (1999).

Honda, H. et al., Oncogene, vol. 18, pp. 3821-3830 (1999).
Liang, T.J. et al., J. Clin. Invest, vol. 97, No. 12, pp. 2872-2877 (1996).
Lee, R.J. et al., Mol. Cell. Biol., vol. 20, No. 2, pp. 672-383 (2000).

* cited by examiner

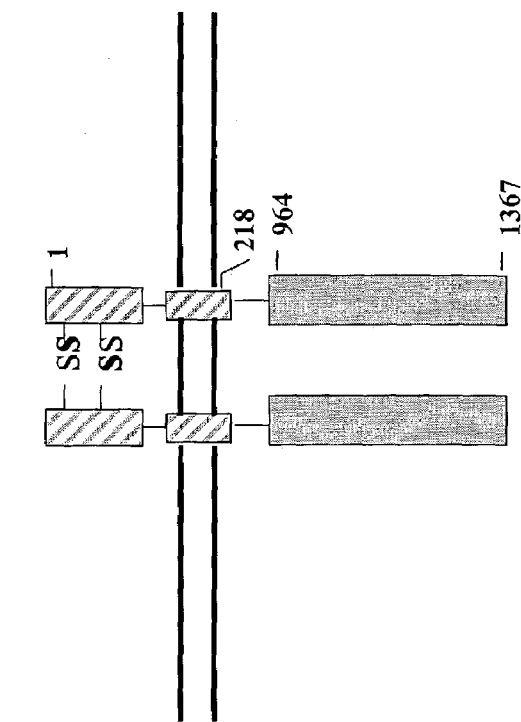
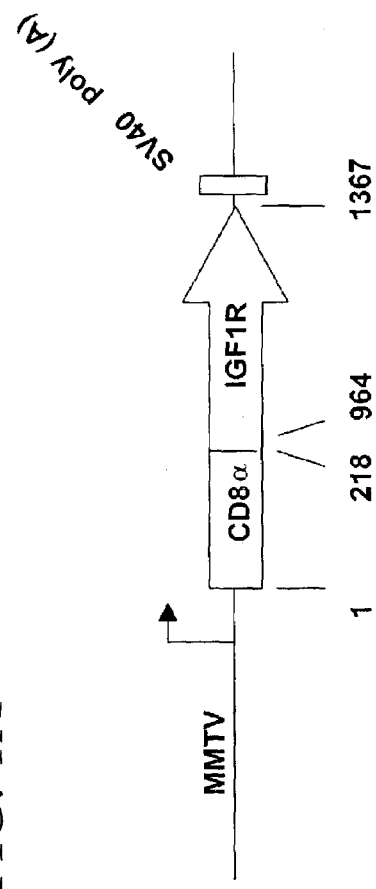
FIG. 1B
FIG. 1A 0.24-9.5 Kb RNA ladder
Control Salivary Gland
MCI line #9 Salivary Gland
MCI line #19 Salivary Gland
MCI line #21 Salivary Gland
MCI line #37 Salivary Gland

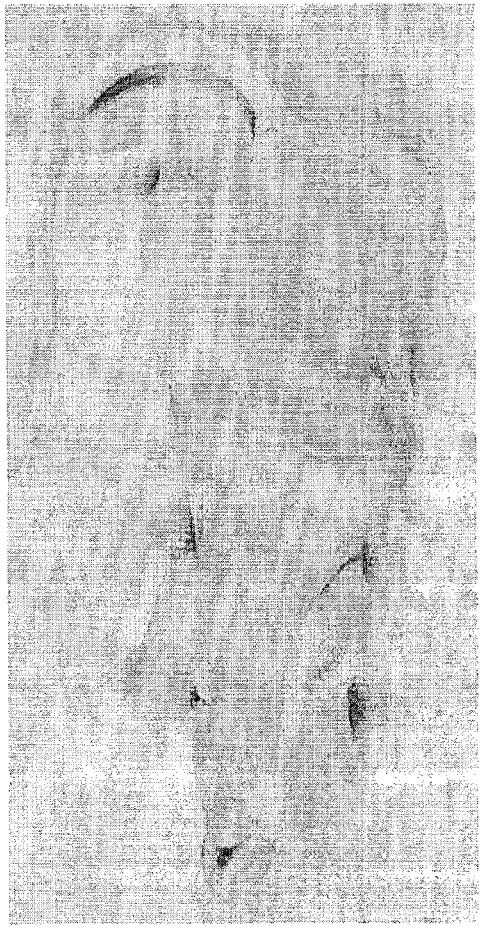
FIG. 8A
FIG. 8B

SEQUENCE LISTING

<160> NUMBER OF SEQ ID NOS: 23

<210> SEQ ID NO 1
<211> LENGTH: 8858
<212> TYPE: DNA
<213> ORGANISM: Homo sapiens

<400> SEQUENCE: 1

```
ttataatggt tacaaataaa gcaatagcat cacaaatttc acaaataaag cattttttc      60 actgcattct agttgtggtt tgtccaaact catcaatgta tcttatcatg tctggatcca    120
ctagttctag agcggccgcc accgcggtgg agctccagct tttgttccct ttagtgaggg    180
ttaatttcga gcttggcgta atcatggtca tagctgtttc ctgtgtgaaa ttgttatccg    240
```

-continued

```
ctcacaattc cacacaacat acgagccgga agcataaagt gtaaagcctg gggtgcctaa    300
tgagtgagct aactcacatt aattgcgttg cgctcactgc ccgctttcca gtcgggaaac    360
ctgtcgtgcc agctgcatta atgaatcggc caacgcgcgg ggagaggcgg tttgcgtatt    420
gggcgctctt ccgcttcctc gctcactgac tcgctgcgct cggtcgttcg ctgcggcga    480 gcggtatcag ctcactcaaa ggcggtaata cggttatcca cagaatcagg gataacgca    540 ggaaagaaca tgtgagcaaa aggccagcaa aaggccagga accgtaaaaa ggccgcgttg    600
ctggcgtttt tccataggct ccgcccccct gacgagcatc acaaaaatcg acgctcaagt    660
cagaggtggc gaaacccgac aggactataa agataccagg cgtttccccc tggaagctcc    720
ctcgtgcgct ctcctgttcc gaccctgccg cttaccggat acctgtccgc ctttctccct    780
tcgggaagcg tggcgctttc tcatagctca cgctgtaggt atctcagttc ggtgtaggtc    840
gttcgctcca agctgggctg tgtgcacgaa ccccccgttc agcccgaccg ctgcgcctta    900
tccggtaact atcgtcttga gtccaacccg gtaagacacg acttatcgcc actggcagca    960
gccactggta acaggattag cagagcgagg tatgtaggcg gtgctacaga gttcttgaag   1020
tggtggccta actacggcta cactagaaga acagtatttg gtatctgcgc tctgctgaag   1080
ccagttacct tcggaaaaag agttggtagc tcttgatccg gcaaacaaac caccgctggt   1140
agcggtggtt tttttgtttg caagcagcag attacgcgca gaaaaaaagg atctcaagaa   1200
gatcctttga tcttttctac ggggtctgac gctcagtgga acgaaaactc acgttaaggg   1260
attttggtca tgagattatc aaaaaggatc ttcacctaga tccttttaaa ttaaaaatga   1320
agttttaaat caatctaaag tatatatgag taaacttggt ctgacagtta ccaatgctta   1380
atcagtgagg cacctatctc agcgatctgt ctatttcgtt catccatagt tgcctgactc   1440
cccgtcgtgt agataactac gatacgggag ggcttaccat ctggccccag tgctgcaatg   1500
ataccgcgag acccacgctc accggctcca gatttatcag caataaacca gccagccgga   1560
agggccgagc gcagaagtgg tcctgcaact ttatccgcct ccatccagtc tattaattgt   1620
tgccgggaag ctagagtaag tagttcgcca gttaatagtt tgcgcaacgt tgttgccatt   1680
gctacaggca tcgtggtgtc acgctcgtcg tttggtatgg cttcattcag ctccggttcc   1740
caacgatcaa ggcgagttac atgatccccc atgttgtgca aaaaagcggt tagctccttc   1800
ggtcctccga tcgttgtcag aagtaagttg gccgcagtgt tatcactcat ggttatggca   1860
gcactgcata attctcttac tgtcatgcca tccgtaagat gcttttctgt gactggtgag   1920
tactcaacca agtcattctg agaatagtgt atgcggcgac cgagttgctc ttgcccggcg   1980
tcaatacggg ataataccgc gccacatagc agaactttaa aagtgctcat cattggaaaa   2040
cgttcttcgg ggcgaaaact ctcaaggatc ttaccgctgt tgagatccag ttcgatgtaa   2100
cccactcgtg cacccaactg atcttcagca tcttttactt tcaccagcgt ttctgggtga   2160
gcaaaaacag gaaggcaaaa tgccgcaaaa aagggaataa gggcgacacg gaaatgttga   2220
atactcatac tcttcctttt tcaatattat tgaagcattt atcagggtta ttgtctcatg   2280
agcggataca tatttgaatg tatttagaaa aataaacaaa tagggggttcc gcgcacattt   2340 ccccgaaaag tgccacctaa attgtaagcg ttaatatttt gttaaaattc gcgttaaatt   2400
tttgttaaat cagctcattt tttaaccaat aggccgaaat cggcaaaatc ccttataaat   2460
caaaagaata accgagata gggttgagtg ttgttccagt ttggaacaag agtccactat   2520
taaagaacgt ggactccaac gtcaaagggc gaaaaaccgt ctatcagggc gatggcccac   2580
```

-continued

```
tacgtgaacc atcaccctaa tcaagttttt tggggtcgag gtgccgtaaa gcactaaatc    2640
ggaaccctaa agggagcccc cgatttagag cttgacgggg aaagccggcg aacgtggcga    2700
gaaaggaagg gaagaaagcg aaaggagcgg gcgctagggc gctggcaagt gtagcggtca    2760
cgctgcgcgt aaccaccaca cccgccgcgc ttaatgcgcc gctacagggc gcgtcccatt    2820
cgccattcag gctgcgcaac tgttgggaag ggcgatcgt gcgggcctct tcgctattac    2880
gccagctggc gaaaggggga tgtgctgcaa ggcgattaag ttgggtaacg ccagggtttt    2940
cccagtcacg acgttgtaaa acgacggcca gtgaattgta atacgactca ctatagggcg    3000
aattgggtac cgggcccccc ctcgaggtcg acgctctccc ttatgcgact cctgcattag    3060
gaagcagccc agtagtaggt tgaggccgtt gagcaccgcc gccgcaagga atggtgcatg    3120
caaggagatg gcgcccaaca gtcccccggc cacggggcct gccaccatac ccacgccgaa    3180
acaagcgctc atgagcccga agtggcgagc ccgatcttcc ccatcggtga tgtcggcgat    3240
ataggcgcca gcaaccgcac ctgtggcgcc ggtgatgccg gccacgatgc gtccggcgta    3300
gaggatccca atgatagaga ttttactgct ctagttcccc atacagaatt gtttcgctta    3360
gttgcagcct caagatatct tattctcaaa aggccaggat ttcaagaaca tgacatgatt    3420
cctacatctg cctgtgttac ttacccttat gccatattat taggattacc tcagctaata    3480
gatatagaga aaagaggatc tacttttcat atttcctgtt cttcttgtag attgactaat    3540
tgtttagatt cttctgccta cgactatgca gcgatcatag tcaagaggcc gccatacgtg    3600
ctgctacctg tagatattgg tgatgaacca tggtttgatg attctgccat tcaaaccttt    3660
aggtatgcca cagatttaat tcgagccaag cgattcgtcg ctgccattat tctgggcata    3720
tctgctttaa ttgctattat cacttccttt gctgtagcta ctactgcttt agttaaggag    3780
atgcaaactg ctacgtttgt taataatctt cataggaatg ttacattagc cttatctgaa    3840
caaagaataa tagattttaaa attagaagct agacttaatg cttagaaga agtagtttta    3900 gagttgggac aagatgtggc aaacttaaag accagaatgt ccaccaggtg tcatgcaaat    3960
tatgatttta tctgcgttac acctttacca tataatgctt ctgagagctg ggaaagaacc    4020
aaagctcatt tattgggcat ttggaatgac aatgagattt catataacat acaagaatta    4080
accaacctga ttagtgatat gagcaaacaa catattgaca cagtggacct cagtggcttg    4140
gctcagtcct tgccaatgg agtaaaggct ttaaatccat tagattggac acaatatttc    4200
atttttatag gtgttggagc cctgctttta gtcatagtgc ttatgatttt ccccattgtt    4260
ttccagtgcc ttgcgaagag ccttgaccaa gtgcagtcag atcttaacgt gcttcttta    4320 aaaaagaaaa aaggggggaaa tgccgcgcct gcagcagaaa tggttgaact cccgagagtg    4380
tcctacacct agggagagaag cagccaaggg gttgttccc accaaggacg acccgtctgc    4440
gcacaaacgg atgagcccat cagacaaaga catattcatt ctctgctgca aacttggcat    4500
agctctgctt tgcctggggc tattggggga agttgcggtt cgtgctcgca gggctctcac    4560
ccttgactct tttaatagct cttctgtgca agattacaat ctaaacaatt cggagaactc    4620
gaccttcctc ctgaggcaag gaccacagcc aacttcctct tacaagccgc atcgattttg    4680
tccttcagaa atagaaataa gaatgcttgc taaaattat attttacca ataagaccaa    4740 tccaataggt agattattag ttactatgtt aagaaatgaa tcattatctt ttagtactat    4800
ttttactcaa attcagaagt tagaaatggg aatagaaaat agaaagagac gctcaacctc    4860
aattgaagaa caggtgcaag gactattgac cacaggccta aagtaaaaa agggaaaaaa    4920 gagtgttttt gtcaaaatag gagacaggtg gtggcaacca gggacttata ggggaccttaa  4980
```

```
catctacaga ccaacagatg ccccttacc atatacagga agatatgact taaattggga    5040
taggtgggtt acagtcaatg ctataaagt gttatataga tccctccctt ttcgtgaaag    5100
actcgccaga gctagacctc cttggtgtat gttgtctcaa gaagaaaaag acgacatgaa    5160
acaacaggta catgattata tttatctagg aacaggaatg cacttttggg gaaagatttt    5220
ccataccaag gaggggacag tggctggact aatagaacat tattctgcaa aaacttatgg    5280
catgagttat tatgaatagc ctttattggc ccaaccttgc ggttcccagg gcttaagtaa    5340
gtttttggtt acaaactgtt cttaaaacga ggatgtgaga caagtggttt cctgacttgg    5400
tttggtatca aaggttctga tctgagctct gagtgttcta ttttcctatg ttcttttgga    5460
atttatccaa atcttatgta aatgcttatg taaaccaaga tataaagag tgctgatttt    5520 ttgagtaaac ttgcaacagt cctaacattc acctcttgtg tgtttgtgtc tgttcgccat    5580
cccgtctccg ctcgtcactt atccttcact ttccagaggg tcccccgca gaccccggcg    5640 tagaggatcc gcacccttga tgactccgtc tgaatttttg gtttcagttt ggtaccgaag    5700
ctgcgcggcg cgtctgcttg ttacttgttt gactgttgga attgtttgtc ttctttgtga    5760
cctgactgtg gttttctgga cgtgttgtgt ctgttagtgt cttttgact tttgtttcgt    5820 gtttgaattt ggactgacga ctgtgtttaa aatcttagac cgacgactgt gtttgaaatc    5880
atgaaactgt ttgctttgtt cgtcgaagag ttttacttgg tccccttaac gcttagtgag    5940
taagaaactt aattttgtag accccgctct agtggcagtg tgttggttga tagccaaagt    6000 taattttttaa aacatagtgt tttgggggtt gggatttag ctcagtgata gagctcttgc    6060
ctagcaagcg caaggccctg ggttcggtcc ccagctctga aaaaaggaa agagaaacaa    6120 aacaaaaaca tatagtgttt tatctgtgct tatgcccgca gcccgagccg cacccgccgc    6180
ggacggagcc catgcgcggg cccagtcggc gcccgtccgc gccccgcccc tgccccggcc    6240
ccggccccca agctgatcta tatcgatatt acgtagataa acttaagctt cgagccaagc    6300
agcgtcctgg ggagcgcgtc atggccttac cagtgaccgc cttgctcctg ccgctggcct    6360
tgctgctcca cgccgccagg ccgagccagt tccgggtgtc gccgctggat cggacctgga    6420
acctgggcga gacagtggag ctgaagtgcc aggtgctgct gtccaacccg acgtcgggct    6480
gctcgtggct cttccagccg cgcggcgccg ccgccagtcc caccttcctc ctataccctct    6540 cccaaaacaa gcccaaggcg gccgaggggc tggacaccca gcggttctcg ggcaagaggt    6600
tgggggacac cttcgtcctc accctgagcg acttccgccg agagaacgag ggctactatt    6660
tctgctcggc cctgagcaac tccatcatgt acttcagcca cttcgtgccg gtcttcctgc    6720
cagcgaagcc caccacgacg ccagcgccgc gaccaccaac accggcgccc accatcgcgt    6780
cgcagcccct gtccctgcgc ccagaggcgt gccggccagc ggcgggggc gcagtgcaca    6840 cgaggggct ggacttcgcc tgtgatatct acatctgggc gcccttggcc gggacttgtg    6900
gggtccttct cctgtcactg gttatcaccc tttactgcaa ccacaggaac cgaagacgtg    6960
tttgcaaatg tccccgatcc aacagcaggc tggggaatgg agtgctgtat gcctctgtga    7020 accccggagta cttcagcgct gctgatgtgt acgttcctga tgagtgggag gtggctcggg    7080
agaagatcac catgagccgg gaacttgggc aggggtcgtt tgggatggtc tatgaaggag    7140
ttgccaaggg tgtggtgaaa gatgaacctg aaaccagagt ggccattaaa acagtgaacg    7200
aggccgcaag catgcgtgag aggattgagt ttctcaacga agcttctgtg atgaaggagt    7260
tcaattgtca ccatgtggtg cgattgctgg gtgtggtgtc ccaaggccag ccaacactgg    7320
```

-continued

| | |
|---|---|
| tcatcatgga actgatgaca cggggcgatc tcaaaagtta tctccggtct ctgaggccag | 7380 |
| aaatggagaa taatccagtc ctagcacctc caagcctgag caagatgatt cagatggccg | 7440 |
| gagagattgc agacggcatg gcatacctca acgccaataa gttcgtccac agagaccttg | 7500 |
| ctgcccggaa ttgcatggta gccgaagatt tcacagtcaa aatcggagat tttggtatga | 7560 |
| cgcgagatat ctatgagaca gactattacc ggaaaggagg gaaagggctg ctgcccgtgc | 7620 |
| gctggatgtc tcctgagtcc ctcaaggatg gagtcttcac cacttactcg gacgtctggt | 7680 |
| ccttcgggt cgtcctctgg gagatcgcca cactggccga gcagccctac cagggcttgt | 7740 |
| ccaacgagca agtccttcgc ttcgtcatgg agggcggcct tctggacaag ccagacaact | 7800 |
| gtcctgacat gctgtttgaa ctgatgcgca tgtgctggca gtataacccc aagatgaggc | 7860 |
| cttccttcct ggagatcatc agcagcatca agaggagat ggagcctggc ttccgggagg | 7920 |
| tctccttcta ctacagcgag gagaacaagc tgcccgagcc ggaggagctg gacctggagc | 7980 |
| cagagaacat ggagagcgtc cccctggacc cctcggcctc tcgtcctcc ctgccactgc | 8040 |
| ccgacagaca ctcaggacac aaggccgaga acggccccgg ccctggggtg ctggtcctcc | 8100 |
| gcgccagctt cgacgagaga cagccttacg cccacatgaa cggggccgc aagaacgagc | 8160 |
| gggccttgcc gctgccccag tcttcgacct gctgatcctt ggatccacta gtccagtgtg | 8220 |
| gtggaattat ctagacttg atatcgaatt cctgcaggtc gcggccgcga ctctagagga | 8280 |
| tctttgtgaa ggaaccttac ttctgtggtg tgacataatt ggacaaacta cctacagaga | 8340 |
| tttaaagctc taaggtaaat ataaaatttt taagtgtata atgtgttaaa ctactgattc | 8400 |
| taattgtttg tgtattttag attccaacct atggaactga tgaatgggag cagtggtgga | 8460 |
| atgcctttaa tgaggaaaac ctgttttgct cagaagaaat gccatctagt gatgatgagg | 8520 |
| ctactgctga ctctcaacat tctactcctc caaaaaagaa gagaaaggta gaagacccca | 8580 |
| aggactttcc ttcagaattg ctaagttttt tgagtcatgc tgtgtttagt aatagaactc | 8640 |
| ttgcttgctt tgctatttac accacaaagg aaaaagctgc actgctatac aagaaaatta | 8700 |
| tggaaaaata tttgatgtat agtgccttga ctagagatca taatcagcca taccacattt | 8760 |
| gtagaggttt tacttgcttt aaaaaacctc ccacacctcc ccctgaacct gaaacataaa | 8820 |
| atgaatgcaa ttgttgttgt taacttgttt attgcagc | 8858 |

<210> SEQ ID NO 2
<211> LENGTH: 692
<212> TYPE: DNA
<213> ORGANISM: Homo sapiens

<400> SEQUENCE: 2

| | |
|---|---|
| agcttcgagc caagcagcgt cctggggagc gcgtcatggc cttaccagtg accgccttgc | 60 |
| tcctgccgct ggccttgctg ctccacgccg ccaggccgag ccagttccgg gtgtcgccgc | 120 |
| tggatcggac ctggaacctg gcgagacag tggagctgaa gtgccaggtg ctgctgtcca | 180 |
| acccgacgtc gggctgctcg tggctcttcc agccgcgcgg cgccgccgcc agtcccacct | 240 |
| tcctcctata cctctcccaa aacaagccca aggcggccga ggggctggac acccagcggt | 300 |
| tctcgggcaa gaggttgggg gacaccttcg tcctcaccct gagcgacttc cgccgagaga | 360 |
| acgagggcta ctatttctgc tcggcccctga gcaactccat catgtacttc agccacttcg | 420 |
| tgccggtctt cctgccagcg aagcccacca cgacgccagc gccgcgacca ccaacaccgg | 480 |
| cgcccaccat cgcgtcgcag cccctgtccc tgcgcccaga ggcgtgccgg ccagcggcgg | 540 |
| ggggcgcagt gcacacgagg gggctggact cgcctgtga tatctacatc tgggcgccct | 600 |

```
tggccgggac ttgtggggtc cttctcctgt cactggttat cacccttac tgcaaccaca    660 ggaaccgaag acgtgtttgc aaatgtcccc gg                                 692
```

<210> SEQ ID NO 3
<211> LENGTH: 219
<212> TYPE: PRT
<213> ORGANISM: Homo sapiens
<400> SEQUENCE: 3

```
Met Ala Leu Pro Val Thr Ala Leu Leu Leu Pro Leu Ala Leu Leu Leu
 1               5                  10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg
    210                 215
```

<210> SEQ ID NO 4
<211> LENGTH: 1214
<212> TYPE: DNA
<213> ORGANISM: Homo sapiens
<400> SEQUENCE: 4

```
acagcaggct ggggaatgga gtgctgtatg cctctgtgaa cccggagtac ttcagcgctg    60
ctgatgtgta cgttcctgat gagtgggagg tggctcggga agatcacc atgagccggg    120 aacttgggca ggggtcgttt gggatggtct atgaaggagt tgccaagggt gtggtgaaag    180
atgaacctga aaccagagtg gccattaaaa cagtgaacga ggccgcaagc atgcgtgaga    240
ggattgagtt tctcaacgaa gcttctgtga tgaaggagtt caattgtcac catgtggtgc    300
gattgctggg tgtggtgtcc caaggccagc caacactggt catcatggaa ctgatgacac    360
ggggcgatct caaaagttat ctccggtctc tgaggccaga aatggagaat aatccagtcc    420
tagcacctcc aagcctgagc aagatgattc agatggccgg agagattgca gacggcatgg    480
```

-continued

```
catacctcaa cgccaataag ttcgtccaca gagaccttgc tgcccggaat tgcatggtag   540
ccgaagattt cacagtcaaa atcggagatt ttggtatgac gcgagatatc tatgagacag   600
actattaccg gaaaggaggc aaagggctgc tgcccgtgcg ctggatgtct cctgagtccc   660
tcaaggatgg agtcttcacc acttactcgg acgtctggtc cttcggggtc gtcctctggg   720
agatcgccac actggccgag cagccctacc agggcttgtc caacgagcaa gtccttcgct   780
tcgtcatgga gggcggcctt ctggacaagc cagacaactg tcctgacatg ctgtttgaac   840
tgatgcgcat gtgctggcag tataacccca agatgaggcc ttccttcctg agatcatca    900 gcagcatcaa agaggagatg gagcctggct tccgggaggt ctccttctac tacagcgagg   960
agaacaagct gcccgagccg gaggagctgg acctggagcc agagaacatg gagagcgtcc  1020
ccctggaccc ctcggcctcc tcgtcctccc tgccactgcc cgacagacac tcaggacaca  1080
aggccgagaa cggccccggc cctggggtgc tggtcctccg cgccagcttc gacgagagac  1140
agccttacgc ccacatgaac ggggccgca agaacgagcg ggccttgccg ctgcccagt    1200 cttcgacctg ctga                                                    1214
```

<210> SEQ ID NO 5
<211> LENGTH: 403
<212> TYPE: PRT
<213> ORGANISM: Homo sapiens

<400> SEQUENCE: 5

```
Ser Arg Leu Gly Asn Gly Val Leu Tyr Ala Ser Val Asn Pro Glu Tyr
1               5                  10                  15

Phe Ser Ala Ala Asp Val Tyr Val Pro Asp Glu Trp Glu Val Ala Arg
            20                  25                  30

Glu Lys Ile Thr Met Ser Arg Glu Leu Gly Gln Gly Ser Phe Gly Met
        35                  40                  45

Val Tyr Glu Gly Val Ala Lys Gly Val Val Lys Asp Glu Pro Glu Thr
    50                  55                  60

Arg Val Ala Ile Lys Thr Val Asn Glu Ala Ala Ser Met Arg Glu Arg
65                  70                  75                  80

Ile Glu Phe Leu Asn Glu Ala Ser Val Met Lys Glu Phe Asn Cys His
                85                  90                  95

His Val Val Arg Leu Leu Gly Val Val Ser Gln Gly Gln Pro Thr Leu
            100                 105                 110

Val Ile Met Glu Leu Met Thr Arg Gly Asp Leu Lys Ser Tyr Leu Arg
        115                 120                 125

Ser Leu Arg Pro Glu Met Glu Asn Asn Pro Val Leu Ala Pro Pro Ser
    130                 135                 140

Leu Ser Lys Met Ile Gln Met Ala Gly Glu Ile Ala Asp Gly Met Ala
145                 150                 155                 160

Tyr Leu Asn Ala Asn Lys Phe Val His Arg Asp Leu Ala Ala Arg Asn
                165                 170                 175

Cys Met Val Ala Glu Asp Phe Thr Val Lys Ile Gly Asp Phe Gly Met
            180                 185                 190

Thr Arg Asp Ile Tyr Glu Thr Asp Tyr Tyr Arg Lys Gly Gly Lys Gly
        195                 200                 205

Leu Leu Pro Val Arg Trp Met Ser Pro Glu Ser Leu Lys Asp Gly Val
    210                 215                 220

Phe Thr Thr Tyr Ser Asp Val Trp Ser Phe Gly Val Val Leu Trp Glu
225                 230                 235                 240
```

```
Ile Ala Thr Leu Ala Glu Gln Pro Tyr Gln Gly Leu Ser Asn Glu Gln
                245                 250                 255
Val Leu Arg Phe Val Met Glu Gly Leu Leu Asp Lys Pro Asp Asn
            260                 265                 270
Cys Pro Asp Met Leu Phe Glu Leu Met Arg Met Cys Trp Gln Tyr Asn
            275                 280                 285
Pro Lys Met Arg Pro Ser Phe Leu Glu Ile Ile Ser Ile Lys Glu
        290                 295                 300
Glu Met Glu Pro Gly Phe Arg Glu Val Ser Phe Tyr Tyr Ser Glu Glu
305                 310                 315                 320
Asn Lys Leu Pro Glu Pro Glu Leu Asp Leu Glu Pro Glu Asn Met
                325                 330                 335
Glu Ser Val Pro Leu Asp Pro Ser Ala Ser Ser Ser Leu Pro Leu
            340                 345                 350
Pro Asp Arg His Ser Gly His Lys Ala Glu Asn Gly Pro Gly Pro Gly
            355                 360                 365
Val Leu Val Leu Arg Ala Ser Phe Asp Glu Arg Gln Pro Tyr Ala His
        370                 375                 380
Met Asn Gly Gly Arg Lys Asn Glu Arg Ala Leu Pro Leu Pro Gln Ser
385                 390                 395                 400
Ser Thr Cys

<210> SEQ ID NO 6
<211> LENGTH: 1995
<212> TYPE: DNA
<213> ORGANISM: Homo sapiens

<400> SEQUENCE: 6
gctagcgttt aaacttaagc ttcgagccaa gcagcgtcct ggggagcgcg tcatggcctt      60
accagtgacc gccttgctcc tgccgctggc cttgctgctc cacgccgcca ggccgagcca     120
gttccgggtg tcgccgctgg atcggacctg gaacctgggc gagacagtgg agctgaagtg     180
ccaggtgctg ctgtccaacc cgacgtcggg ctgctcgtgg ctcttccagc gcgcggcgc     240
cgccgccagt cccaccttcc tcctataccc tcccaaaaac aagcccaagg cggccgaggg     300
gctggacacc cagcggttct cgggcaagag gttgggggac accttcgtcc tcaccctgag     360
cgacttccgc cgagagaacg agggctacta tttctgctcg gccctgagca actccatcat     420
gtacttcagc cacttcgtgc cggtcttcct gccagcgaag cccaccacga cgccagcgcc     480
gcgaccacca acaccggcgc ccaccatcgc gtcgcagccc ctgtccctgc gcccagaggc     540
gtgccggcca gcggcggggg gcgcagtgca cacgaggggg ctggacttcg cctgtgatat     600
ctacatctgg gcgcccttgg ccgggacttg tgggtccttc tcctgtcac tggttatcac     660
ccttactgc aaccacagga accgaagacg tgtttgcaaa tgtccccgga tccacagcag     720
gctgggaat ggagtgctgt atgcctctgt gaacccggag tacttcagcg ctgctgatgt     780
gtacgttcct gatgagtggg aggtggctcg ggagaagatc accatgagcc gggaacttgg     840
gcaggggtcg tttgggatgg tctatgaagg agttgccaag ggtgtggtga agatgaacc     900
tgaaaccaga gtggccatta aaacagtgaa cgaggccgca agcatgcgtg agaggattga     960
gtttctcaac gaagcttctg tgatgaagga gttcaattgt caccatgtgg tgcgattgct    1020
gggtgtggtg tcccaaggcc agccaacact ggtcatcatg gaactgatga cacggggcga    1080
tctcaaaagt tatctccggt ctctgaggcc agaaatggag aataatccag tcctagcacc    1140
tccaagcctg agcaagatga ttcagatggc cggagagatt gcagacggca tggcatacct    1200
```

```
caacgccaat aagttcgtcc acagagacct tgctgcccgg aattgcatgg tagccgaaga      1260
tttcacagtc aaaatcggag attttggtat gacgcgagat atctatgaga cagactatta      1320
ccggaaagga ggsaaagggc tgctgcccgt gcgctggatg tctcctgagt ccctcaagga      1380
tggagtcttc accacttact cggacgtctg gtccttcggg gtcgtcctct gggagatcgc      1440
cacactggcc gagcagccct accagggctt gtccaacgag caagtccttc gcttcgtcat      1500
ggagggcggc cttctggaca agccagacaa ctgtcctgac atgctgtttg aactgatgcg      1560
catgtgctgg cagtataacc ccaagatgag gccttccttc ctggagatca tcagcagcat      1620
caaagaggag atggagcctg gcttccggga ggtctccttc tactacagcg aggagaacaa      1680
gctgcccgag ccgagggagc tggacctgga gccagagaac atggagagcg tcccctgga       1740 ccccctcggcc tcctcgtcct ccctgccact gcccgacaga cactcaggac acaaggccga     1800
gaacggcccc ggccctgggg tgctggtcct ccgcgccagc ttcgacgaga gacagcctta     1860
cgcccacatg aacgggggcc gcaagaacga gcgggccttg ccgctgcccc agtcttcgac     1920
ctgctgagga tccactagtc cagtgtggtg gaattctgca gatatccagc acagtggcgg    1980
ccgctcgagt ctaga                                                     1995

<210> SEQ ID NO 7
<211> LENGTH: 624
<212> TYPE: PRT
<213> ORGANISM: Homo sapiens

<400> SEQUENCE: 7

Met Ala Leu Pro Val Thr Ala Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
        50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Ile His Ser Arg Leu
    210                 215                 220
```

-continued

```
Gly Asn Gly Val Leu Tyr Ala Ser Val Asn Pro Glu Tyr Phe Ser Ala
225                 230                 235                 240

Ala Asp Val Tyr Val Pro Asp Glu Trp Glu Val Ala Arg Glu Lys Ile
            245                 250                 255

Thr Met Ser Arg Glu Leu Gly Gln Gly Ser Phe Gly Met Val Tyr Glu
        260                 265                 270

Gly Val Ala Lys Gly Val Val Lys Asp Glu Pro Glu Thr Arg Val Ala
    275                 280                 285

Ile Lys Thr Val Asn Glu Ala Ala Ser Met Arg Glu Arg Ile Glu Phe
290                 295                 300

Leu Asn Glu Ala Ser Val Met Lys Glu Phe Asn Cys His His Val Val
305                 310                 315                 320

Arg Leu Leu Gly Val Val Ser Gln Gly Gln Pro Thr Leu Val Ile Met
            325                 330                 335

Glu Leu Met Thr Arg Gly Asp Leu Lys Ser Tyr Leu Arg Ser Leu Arg
        340                 345                 350

Pro Glu Met Glu Asn Asn Pro Val Leu Ala Pro Pro Ser Leu Ser Lys
    355                 360                 365

Met Ile Gln Met Ala Gly Glu Ile Ala Asp Gly Met Ala Tyr Leu Asn
370                 375                 380

Ala Asn Lys Phe Val His Arg Asp Leu Ala Ala Arg Asn Cys Met Val
385                 390                 395                 400

Ala Glu Asp Phe Thr Val Lys Ile Gly Asp Phe Gly Met Thr Arg Asp
            405                 410                 415

Ile Tyr Glu Thr Asp Tyr Tyr Arg Lys Gly Gly Lys Gly Leu Leu Pro
        420                 425                 430

Val Arg Trp Met Ser Pro Glu Ser Leu Lys Asp Gly Val Phe Thr Thr
    435                 440                 445

Tyr Ser Asp Val Trp Ser Phe Gly Val Val Leu Trp Glu Ile Ala Thr
450                 455                 460

Leu Ala Glu Gln Pro Tyr Gln Gly Leu Ser Asn Glu Gln Val Leu Arg
465                 470                 475                 480

Phe Val Met Glu Gly Gly Leu Leu Asp Lys Pro Asp Asn Cys Pro Asp
            485                 490                 495

Met Leu Phe Glu Leu Met Arg Met Cys Trp Gln Tyr Asn Pro Lys Met
        500                 505                 510

Arg Pro Ser Phe Leu Glu Ile Ile Ser Ser Ile Lys Glu Glu Met Glu
    515                 520                 525

Pro Gly Phe Arg Glu Val Ser Phe Tyr Tyr Ser Glu Glu Asn Lys Leu
530                 535                 540

Pro Glu Pro Glu Glu Leu Asp Leu Glu Pro Glu Asn Met Glu Ser Val
545                 550                 555                 560

Pro Leu Asp Pro Ser Ala Ser Ser Ser Ser Leu Pro Leu Pro Asp Arg
            565                 570                 575

His Ser Gly His Lys Ala Glu Asn Gly Pro Gly Pro Gly Val Leu Val
        580                 585                 590

Leu Arg Ala Ser Phe Asp Glu Arg Gln Pro Tyr Ala His Met Asn Gly
    595                 600                 605

Gly Arg Lys Asn Glu Arg Ala Leu Pro Leu Pro Gln Ser Ser Thr Cys
610                 615                 620

<210> SEQ ID NO 8
<211> LENGTH: 21
<212> TYPE: DNA
```

<213> ORGANISM: Homo sapiens

<400> SEQUENCE: 8

| agggtgtggt gaaagatgaa c | 21 |

<210> SEQ ID NO 9
<211> LENGTH: 21
<212> TYPE: DNA
<213> ORGANISM: Homo sapiens

<400> SEQUENCE: 9

| cgtccgagta agtggtgaag a | 21 |

<210> SEQ ID NO 10
<211> LENGTH: 2411
<212> TYPE: DNA
<213> ORGANISM: Homo sapiens

<400> SEQUENCE: 10

| agcttcgagc caagcagcgt cctggggagc gcgtcatggc cttaccagtg accgccttgc | 60 |
| tcctgccgct ggccttgctg ctccacgccg ccaggccgag ccagttccgg gtgtcgccgc | 120 |
| tggatcggac ctggaacctg gcgagacag tggagctgaa gtgccaggtg ctgctgtcca | 180 |
| acccgacgtc gggctgctcg tggctcttcc agccgcgcgg cgccgccgcc agtcccacct | 240 |
| tcctcctata cctctcccaa aacaagccca aggcggccga ggggctggac acccagcggt | 300 |
| tctcgggcaa gaggttgggg gacaccttcg tcctcaccct gagcgacttc cgccgagaga | 360 |
| cgagggcta ctatttctgc tcggccctga gcaactccat catgtacttc agccacttcg | 420 |
| tgccggtctt cctgccagcg aagcccacca cgacgccagc gccgcgacca ccaacaccgg | 480 |
| cgcccaccat cgcgtcgcag cccctgtccc tgcgcccaga ggcgtgccgg ccagcggcgg | 540 |
| ggggcgcagt gcacacgagg gggctggact tcgcctgtga tatctacatc tgggcgccct | 600 |
| tggccgggac ttgtggggtc cttctcctgt cactggttat cacccttttac tgcaaccaca | 660 |
| ggaaccgaag acgtgttttgc aaatgtcccc tcgagtctac gatgcggaga ctgctgcagg | 720 |
| aaacggagct ggtggagccg ctgacaccta gcggagcgat gcccaaccag gcgcagatgc | 780 |
| ggatcctgaa agagacggag ctgaggaagg tgaaggtgct tggatctggc gcttttggca | 840 |
| cagtctacaa gggcatctgg atccctgatg gggagaatgt gaaaattcca gtggccatca | 900 |
| aagtgttgag ggaaaacaca tcccccaaag ccaacaaaga aatcttagac gaagcatacg | 960 |
| tgatggctgg tgtgggctcc ccatatgtct cccgccttct gggcatctgc ctgacatcca | 1020 |
| cggtgcagct ggtgacacag cttatgccct atggctgcct cttagaccat gtccgggaaa | 1080 |
| accgcgacg cctgggctcc caggacctgc tgaactggtg tatgcagatt gccaagggga | 1140 |
| tgagctacct ggaggatgtg cggctcgtac acagggactt ggccgctcgg aacgtgctgg | 1200 |
| tcaagagtcc caaccatgtc aaaattacag acttcgggct ggctcggctg ctggacattg | 1260 |
| acgagacaga gtaccatgca gatgggggca aggtgcccat caagtggatg gcgctggagt | 1320 |
| ccattctccg ccggcggttc acccaccaga gtgatgtgtg gagttatggt gtgactgtgt | 1380 |
| gggagctgat gacttttggg gccaaacctt acgatgggat cccagcccgg gagatccctg | 1440 |
| acctgctgga aaaggggag cggctgcccc agccccccat ctgcaccatt gatgtctaca | 1500 |
| tgatcatggt caaatgttgg atgattgact ctgaatgtcg gccaagattc cgggagttgg | 1560 |
| tgtctgaatt ctcccgcatg gccagggacc ccagcgctt tgtggtcatc cagaatgagg | 1620 |
| acttgggccc agccagtccc ttggacagca ccttctaccg ctcactgctg gaggacgatg | 1680 |

```
acatggggga cctggtggat gctgaggagt atctggtacc ccagcagggc ttcttctgtc    1740
cagaccctgc cccgggcgct gggggcatgg tccaccacag gcaccgcagc tcatctacca    1800
ggagtggcgg tggggacctg acactagggc tggagccctc tgaagaggag gcccccaggt    1860
ctccactggc accctccgaa ggggctggct ccgatgtatt tgatggtgac ctgggaatgg    1920
gggcagccaa ggggctgcaa agcctcccca cacatgaccc cagccctcta cagcggtaca    1980
gtgaggaccc cacagtaccc ctgccctctg agactgatgg ctacgttgcc cccctgacct    2040
gcagccccca gcctgaatat gtgaaccagc cagatgttcg gccccagccc ccttcgcccc    2100
gagagggccc tctgcctgct gcccgacctg ctggtgccac tctggaaagg cccaagactc    2160 tctcccagg gaagaatggg gtcgtcaaag acgtttttgc ctttgggggt gccgtggaga    2220
accccgagta cttgacaccc cagggaggag ctgcccctca gccccaccct cctcctgcct    2280
tcagcccagc cttcgacaac ctctattact gggaccagga cccaccgag cgggggggctc    2340 cacccagcac cttcaaaggg acacctacgg cagagaaccc agagtacctg ggtctggacg    2400
tgccagtgtg a                                                        2411
```

```
<210> SEQ ID NO 11
<211> LENGTH: 791
<212> TYPE: PRT
<213> ORGANISM: Homo sapiens

<400> SEQUENCE: 11

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Leu Glu Ser Thr Met Arg
    210                 215                 220

Arg Leu Leu Gln Glu Thr Glu Leu Val Glu Pro Leu Thr Pro Ser Gly
225                 230                 235                 240
```

-continued

```
Ala Met Pro Asn Gln Ala Gln Met Arg Ile Leu Lys Glu Thr Glu Leu
                245                 250                 255

Arg Lys Val Lys Val Leu Gly Ser Gly Ala Phe Gly Thr Val Tyr Lys
            260                 265                 270

Gly Ile Trp Ile Pro Asp Gly Glu Asn Val Lys Ile Pro Val Ala Ile
        275                 280                 285

Lys Val Leu Arg Glu Asn Thr Ser Pro Lys Ala Asn Lys Glu Ile Leu
    290                 295                 300

Asp Glu Ala Tyr Val Met Ala Gly Val Gly Ser Pro Tyr Val Ser Arg
305                 310                 315                 320

Leu Leu Gly Ile Cys Leu Thr Ser Thr Val Gln Leu Val Thr Gln Leu
                325                 330                 335

Met Pro Tyr Gly Cys Leu Leu Asp His Val Arg Glu Asn Arg Gly Arg
            340                 345                 350

Leu Gly Ser Gln Asp Leu Leu Asn Trp Cys Met Gln Ile Ala Lys Gly
        355                 360                 365

Met Ser Tyr Leu Glu Asp Val Arg Leu Val His Arg Asp Leu Ala Ala
    370                 375                 380

Arg Asn Val Leu Val Lys Ser Pro Asn His Val Lys Ile Thr Asp Phe
385                 390                 395                 400

Gly Leu Ala Arg Leu Leu Asp Ile Asp Glu Thr Glu Tyr His Ala Asp
                405                 410                 415

Gly Gly Lys Val Pro Ile Lys Trp Met Ala Leu Glu Ser Ile Leu Arg
            420                 425                 430

Arg Arg Phe Thr His Gln Ser Asp Val Trp Ser Tyr Gly Val Thr Val
        435                 440                 445

Trp Glu Leu Met Thr Phe Gly Ala Lys Pro Tyr Asp Gly Ile Pro Ala
    450                 455                 460

Arg Glu Ile Pro Asp Leu Leu Glu Lys Gly Glu Arg Leu Pro Gln Pro
465                 470                 475                 480

Pro Ile Cys Thr Ile Asp Val Tyr Met Ile Met Val Lys Cys Trp Met
                485                 490                 495

Ile Asp Ser Glu Cys Arg Pro Arg Phe Arg Glu Leu Val Ser Glu Phe
            500                 505                 510

Ser Arg Met Ala Arg Asp Pro Gln Arg Phe Val Val Ile Gln Asn Glu
        515                 520                 525

Asp Leu Gly Pro Ala Ser Pro Leu Asp Ser Thr Phe Tyr Arg Ser Leu
    530                 535                 540

Leu Glu Asp Asp Asp Met Gly Asp Leu Val Asp Ala Glu Glu Tyr Leu
545                 550                 555                 560

Val Pro Gln Gln Gly Phe Phe Cys Pro Asp Pro Ala Pro Gly Ala Gly
                565                 570                 575

Gly Met Val His His Arg His Arg Ser Ser Ser Thr Arg Ser Gly Gly
            580                 585                 590

Gly Asp Leu Thr Leu Gly Leu Glu Pro Ser Glu Glu Glu Ala Pro Arg
        595                 600                 605

Ser Pro Leu Ala Pro Ser Glu Gly Ala Gly Ser Asp Val Phe Asp Gly
    610                 615                 620

Asp Leu Gly Met Gly Ala Ala Lys Gly Leu Gln Ser Leu Pro Thr His
625                 630                 635                 640

Asp Pro Ser Pro Leu Gln Arg Tyr Ser Glu Asp Pro Thr Val Pro Leu
                645                 650                 655
```

```
Pro Ser Glu Thr Asp Gly Tyr Val Ala Pro Leu Thr Cys Ser Pro Gln
            660                 665                 670

Pro Glu Tyr Val Asn Gln Pro Asp Val Arg Pro Gln Pro Pro Ser Pro
        675                 680                 685

Arg Glu Gly Pro Leu Pro Ala Ala Arg Pro Ala Gly Ala Thr Leu Glu
    690                 695                 700

Arg Pro Lys Thr Leu Ser Pro Gly Lys Asn Gly Val Val Lys Asp Val
705                 710                 715                 720

Phe Ala Phe Gly Gly Ala Val Glu Asn Pro Glu Tyr Leu Thr Pro Gln
                725                 730                 735

Gly Gly Ala Ala Pro Gln Pro His Pro Pro Ala Phe Ser Pro Ala
            740                 745                 750

Phe Asp Asn Leu Tyr Tyr Trp Asp Gln Asp Pro Glu Arg Gly Ala
            755                 760                 765

Pro Pro Ser Thr Phe Lys Gly Thr Pro Thr Ala Glu Asn Pro Glu Tyr
    770                 775                 780

Leu Gly Leu Asp Val Pro Val
785                 790

<210> SEQ ID NO 12
<211> LENGTH: 690
<212> TYPE: DNA
<213> ORGANISM: Homo sapiens

<400> SEQUENCE: 12
agcttcgagc caagcagcgt cctggggagc gcgtcatggc cttaccagtg accgccttgc      60
tcctgccgct ggccttgctg ctccacgccg ccaggccgag ccagttccgg gtgtcgccgc     120
tggatcggac ctggaacctg ggcgagacag tggagctgaa gtgccaggtg ctgctgtcca     180
acccgacgtc gggctgctcg tggctcttcc agccgcgcgg cgccgccgcc agtcccacct     240
tcctcctata cctctcccaa aacaagccca aggcggccga ggggctggac acccagcggt     300
tctcgggcaa gaggttgggg gacaccttcg tcctcaccct gagcgacttc gccgagaga      360 acgaggcta ctatttctgc tcggccctga gcaactccat catgtacttc agccacttcg     420
tgccggtctt cctgccagcg aagcccacca cgacgccagc gccgcgacca ccaacaccgg     480
cgcccaccat cgcgtcgcag cccctgtccc tgcgcccaga ggcgtgccgg ccagcggcgg     540
ggggcgcagt gcacacgagg gggctggact cgcctgtga tatctacatc tgggcgccct     600
tggccgggac ttgtgggtc cttctcctgt cactggttat caccctttac tgcaaccaca     660
ggaaccgaag acgtgtttgc aaatgtcccc                                    690

<210> SEQ ID NO 13
<211> LENGTH: 219
<212> TYPE: PRT
<213> ORGANISM: Homo sapiens

<400> SEQUENCE: 13

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60
```

```
Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Leu
    210                 215

<210> SEQ ID NO 14
<211> LENGTH: 1713
<212> TYPE: DNA
<213> ORGANISM: Homo sapiens

<400> SEQUENCE: 14
acgatgcgga gactgctgca ggaaacggag ctggtggagc cgctgacacc tagcggagcg      60
atgcccaacc aggcgcagat gcggatcctg aaagagacgg agctgaggaa ggtgaaggtg     120
cttggatctg cgcttttgg cacagtctac aagggcatct ggatccctga tgggagaat      180 gtgaaaattc cagtggccat caaagtgttg agggaaaaca catcccccaa agccaacaaa     240
gaaatcttag acgaagcata cgtgatggct ggtgtgggct ccccatatgt ctcccgcctt     300
ctgggcatct gcctgacatc cacggtgcag ctggtgacac agcttatgcc ctatggctgc     360
ctcttagacc atgtccggga aaaccgcgga cgcctgggct cccaggacct gctgaactgg     420
tgtatgcaga ttgccaaggg gatgagctac ctggaggatg tgcggctcgt acacagggac     480
ttggccgctc ggaacgtgct ggtcaagagt cccaaccatg tcaaaattac agacttcggg     540
ctggctcggc tgctggacat tgacgagaca gagtaccatg cagatggggg caaggtgccc     600
atcaagtgga tggcgctgga gtccattctc cgccggcggt tcacccacca gagtgatgtg     660
tggagttatg gtgtgactgt gtgggagctg atgacttttg ggccaaaacc ttacgatggg     720
atcccagccc gggagatccc tgacctgctg gaaaaggggg agcggctgcc ccagcccccc     780
atctgcacca ttgatgtcta catgatcatg gtcaaatgtt ggatgattga ctctgaatgt     840
cggccaagat tccgggagtt ggtgtctgaa ttctcccgca tggccaggga ccccagcgc      900 tttgtggtca tccagaatga ggacttgggc ccagccagtc ccttggacag caccttctac     960
cgctcactgc tggaggacga tgacatgggg gacctggtgg atgctgagga gtatctggta    1020
ccccagcagg gcttcttctg tccagaccct gccccgggcg ctgggggcat ggtccaccac    1080
aggcaccgca gctcatctac caggagtggc ggtgggacc tgacactagg gctggagccc    1140
tctgaagagg aggcccccag gtctccactg gcacctccg aaggggctgg ctccgatgta    1200
tttgatggtg acctgggaat ggggcagcc aaggggctgc aaagcctccc cacacatgac    1260
```

-continued

```
cccagccctc tacagcggta cagtgaggac cccacagtac ccctgccctc tgagactgat      1320
ggctacgttg ccccctgac ctgcagcccc cagcctgaat atgtgaacca gccagatgtt      1380 cggcccagc cccttcgcc ccgagagggc cctctgcctg ctgcccgacc tgctggtgcc       1440
actctggaaa ggcccaagac tctctcccca gggaagaatg gggtcgtcaa agacgttttt     1500
gcctttgggg gtgccgtgga aaccccgag tacttgacac cccagggagg agctgccct       1560 cagccccacc ctcctcctgc cttcagccca gccttcgaca acctctatta ctgggaccag    1620
gacccaccag agcggggggc tccacccagc accttcaaag ggacacctac ggcagagaac    1680
ccagagtacc tgggtctgga cgtgccagtg tga                                  1713
```

<210> SEQ ID NO 15
<211> LENGTH: 570
<212> TYPE: PRT
<213> ORGANISM: Homo sapiens

<400> SEQUENCE: 15

```
Thr Met Arg Arg Leu Leu Gln Glu Thr Glu Leu Val Glu Pro Leu Thr
1               5                   10                  15

Pro Ser Gly Ala Met Pro Asn Gln Ala Gln Met Arg Ile Leu Lys Glu
            20                  25                  30

Thr Glu Leu Arg Lys Val Lys Val Leu Gly Ser Gly Ala Phe Gly Thr
        35                  40                  45

Val Tyr Lys Gly Ile Trp Ile Pro Asp Gly Glu Asn Val Lys Ile Pro
50                  55                  60

Val Ala Ile Lys Val Leu Arg Glu Asn Thr Ser Pro Lys Ala Asn Lys
65                  70                  75                  80

Glu Ile Leu Asp Glu Ala Tyr Val Met Ala Gly Val Gly Ser Pro Tyr
                85                  90                  95

Val Ser Arg Leu Leu Gly Ile Cys Leu Thr Ser Thr Val Gln Leu Val
            100                 105                 110

Thr Gln Leu Met Pro Tyr Gly Cys Leu Leu Asp His Val Arg Glu Asn
        115                 120                 125

Arg Gly Arg Leu Gly Ser Gln Asp Leu Leu Asn Trp Cys Met Gln Ile
    130                 135                 140

Ala Lys Gly Met Ser Tyr Leu Glu Asp Val Arg Leu Val His Arg Asp
145                 150                 155                 160

Leu Ala Ala Arg Asn Val Leu Val Lys Ser Pro Asn His Val Lys Ile
                165                 170                 175

Thr Asp Phe Gly Leu Ala Arg Leu Leu Asp Ile Asp Glu Thr Glu Tyr
            180                 185                 190

His Ala Asp Gly Gly Lys Val Pro Ile Lys Trp Met Ala Leu Glu Ser
        195                 200                 205

Ile Leu Arg Arg Arg Phe Thr His Gln Ser Asp Val Trp Ser Tyr Gly
    210                 215                 220

Val Thr Val Trp Glu Leu Met Thr Phe Gly Ala Lys Pro Tyr Asp Gly
225                 230                 235                 240

Ile Pro Ala Arg Glu Ile Pro Asp Leu Leu Glu Lys Gly Glu Arg Leu
                245                 250                 255

Pro Gln Pro Pro Ile Cys Thr Ile Asp Val Tyr Met Ile Met Val Lys
            260                 265                 270

Cys Trp Met Ile Asp Ser Glu Cys Arg Pro Arg Phe Arg Glu Leu Val
        275                 280                 285
```

```
Ser Glu Phe Ser Arg Met Ala Arg Asp Pro Gln Arg Phe Val Val Ile
    290                 295                 300

Gln Asn Glu Asp Leu Gly Pro Ala Ser Pro Leu Asp Ser Thr Phe Tyr
305                 310                 315                 320

Arg Ser Leu Leu Glu Asp Asp Met Gly Asp Leu Val Asp Ala Glu
                325                 330                 335

Glu Tyr Leu Val Pro Gln Gln Gly Phe Phe Cys Pro Asp Pro Ala Pro
                340                 345                 350

Gly Ala Gly Gly Met Val His His Arg His Arg Ser Ser Thr Arg
                355                 360                 365

Ser Gly Gly Gly Asp Leu Thr Leu Gly Leu Glu Pro Ser Glu Glu
370                 375                 380

Ala Pro Arg Ser Pro Leu Ala Pro Ser Glu Gly Ala Gly Ser Asp Val
385                 390                 395                 400

Phe Asp Gly Asp Leu Gly Met Gly Ala Ala Lys Gly Leu Gln Ser Leu
                405                 410                 415

Pro Thr His Asp Pro Ser Pro Leu Gln Arg Tyr Ser Glu Asp Pro Thr
                420                 425                 430

Val Pro Leu Pro Ser Glu Thr Asp Gly Tyr Val Ala Pro Leu Thr Cys
                435                 440                 445

Ser Pro Gln Pro Glu Tyr Val Asn Gln Pro Asp Val Arg Pro Gln Pro
450                 455                 460

Pro Ser Pro Arg Glu Gly Pro Leu Pro Ala Ala Arg Pro Ala Gly Ala
465                 470                 475                 480

Thr Leu Glu Arg Pro Lys Thr Leu Ser Pro Gly Lys Asn Gly Val Val
                485                 490                 495

Lys Asp Val Phe Ala Phe Gly Gly Ala Val Glu Asn Pro Glu Tyr Leu
                500                 505                 510

Thr Pro Gln Gly Gly Ala Ala Pro Gln Pro His Pro Pro Pro Ala Phe
                515                 520                 525

Ser Pro Ala Phe Asp Asn Leu Tyr Tyr Trp Asp Gln Asp Pro Pro Glu
530                 535                 540

Arg Gly Ala Pro Pro Ser Thr Phe Lys Gly Thr Pro Thr Ala Glu Asn
545                 550                 555                 560

Pro Glu Tyr Leu Gly Leu Asp Val Pro Val
                565                 570

<210> SEQ ID NO 16
<211> LENGTH: 9
<212> TYPE: DNA
<213> ORGANISM: Homo sapiens

<400> SEQUENCE: 16 ctcgagtct                                                                 9

<210> SEQ ID NO 17
<211> LENGTH: 1987
<212> TYPE: DNA
<213> ORGANISM: Homo sapiens

<400> SEQUENCE: 17
aagcttcgag ccaagcagcg tcctggggag cgcgtcatgg ccttaccagt gaccgccttg      60
ctcctgccgc tggccttgct gctccacgcc gccaggccga ccagttccg ggtgtcgccg      120 ctggatcgga cctggaacct gggcgagaca gtggagctga agtgccaggt gctgctgtcc     180
aaccccgacg tcggggctgctc gtggctcttc cagccgcgcg gcgccgccgc cagtcccacc     240
```

-continued

```
ttcctcctat acctctccca aaacaagccc aaggcggccg aggggctgga cacccagcgg    300
ttctcgggca agaggttggg ggacaccttc gtcctcaccc tgagcgactt ccgccgagag    360
aacgagggct actatttctg ctcggccctg agcaactcca tcatgtactt cagccacttc    420
gtgccggtct tcctgccagc gaagcccacc acgacgccag cgccgcgacc accaacaccg    480
gcgcccacca tcgcgtcgca gcccctgtcc ctgcgcccag aggcgtgccg gccagcggcg    540
ggggcgcag tgcacacgag ggggctggac ttcgcctgtg atatctacat ctgggcgccc    600
ttggccggga cttgtggggt ccttctcctg tcactggtta tcaccctta ctgcaaccac    660
aggaaccgaa gacgtgtttg caaatgtccc ggatccggca gtgaattagt tcgctacgat    720
gcaagagtac acactcctca tttggatagg cttgtaagtg cccgaagtgt aagcccaact    780
acagaaatgg tttcaaatga atctgtagac taccgagcta cttttccaga agatcagttt    840
cctaattcat ctcagaacgg ttcatgccga caagtgcagt atcctctgac agacatgtcc    900
cccatcctaa ctagtgggga ctctgatata tccagtccat tactgcaaaa tactgtccac    960
attgacctca gtgctctaaa tccagagctg gtccaggcag tgcagcatgt agtgattggg   1020
cccagtagcc tgattgtgca tttcaatgaa gtcataggaa gagggcattt tggttgtgta   1080
tatcatggga ctttgttgga caatgatggc aagaaaattc actgtgctgt gaaatccttg   1140
aacagaatca ctgacatagg agaagtttcc caatttctga ccgagggaat catcatgaaa   1200
gattttagtc atcccaatgt cctctcgctc ctgggaatct gcctgcgaag tgaagggtct   1260
ccgctggtgg tcctaccata catgaaacat ggagatcttc gaaatttcat tcgaaatgag   1320
actcataatc caactgtaaa agatcttatt ggctttggtc ttcaagtagc caaagcgatg   1380
aaatatcttg caagcaaaaa gttttgtccac agagacttgg ctgcaagaaa ctgtatgctg   1440
gatgaaaaat tcacagtcaa ggttgctgat tttggtcttg ccagagacat gtatgataaa   1500
gaatactata gtgtacacaa caaaacaggt gcaaagctgc cagtgaagtg gatggctttg   1560
gaaagtctgc aaactcaaaa gtttaccacc aagtcagatg tgtggtcctt ggcgtcgtc    1620
ctctgggagc tgatgacaag aggagcccca cctatcctg acgtaaacac ctttgatata    1680
actgtttact tgttgcaagg gagaagactc ctacaacccg aatactgccc agaccccta    1740
tatgaagtaa tgctaaaatg ctggcaccct aaagccgaaa tgcgcccatc cttttctgaa   1800
ctggtgtccc ggatatcagc gatcttctct actttcattg gggagcacta tgtccatgtg   1860
aacgctactt atgtgaacgt aaaatgtgtc gctccgtatc cttctctgtt gtcatcagaa   1920
gataacgctg atgatgaggt ggacacacga ccagcctcct tctgggagac atcatagtgc   1980
tagtact                                                              1987
```

<210> SEQ ID NO 18
<211> LENGTH: 646
<212> TYPE: PRT
<213> ORGANISM: Homo sapiens

<400> SEQUENCE: 18

```
Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
            35                  40                  45

Asn Pro Thr Ser Gly Cys Ser Trp Leu Phe Gln Pro Arg Gly Ala Ala
```

```
                  50                  55                  60
Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                     85                  90                  95

Thr Phe Val Leu Thr Leu Ser Asp Phe Arg Arg Glu Asn Glu Gly Tyr
                    100                 105                 110

Tyr Phe Cys Ser Ala Leu Ser Asn Ser Ile Met Tyr Phe Ser His Phe
                115                 120                 125

Val Pro Val Phe Leu Pro Ala Lys Pro Thr Thr Thr Pro Ala Pro Arg
130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
                195                 200                 205

Arg Asn Arg Arg Arg Val Cys Lys Cys Pro Gly Ser Gly Ser Glu Leu
210                 215                 220

Val Arg Tyr Asp Ala Arg Val His Thr Pro His Leu Asp Arg Leu Val
225                 230                 235                 240

Ser Ala Arg Ser Val Ser Pro Thr Thr Glu Met Val Ser Asn Glu Ser
                245                 250                 255

Val Asp Tyr Arg Ala Thr Phe Pro Glu Asp Gln Phe Pro Asn Ser Ser
                260                 265                 270

Gln Asn Gly Ser Cys Arg Gln Val Gln Tyr Pro Leu Thr Asp Met Ser
                275                 280                 285

Pro Ile Leu Thr Ser Gly Asp Ser Asp Ile Ser Ser Pro Leu Leu Gln
290                 295                 300

Asn Thr Val His Ile Asp Leu Ser Ala Leu Asn Pro Glu Leu Val Gln
305                 310                 315                 320

Ala Val Gln His Val Val Ile Gly Pro Ser Ser Leu Ile Val His Phe
                325                 330                 335

Asn Glu Val Ile Gly Arg Gly His Phe Gly Cys Val Tyr His Gly Thr
                340                 345                 350

Leu Leu Asp Asn Asp Gly Lys Lys Ile His Cys Ala Val Lys Ser Leu
                355                 360                 365

Asn Arg Ile Thr Asp Ile Gly Glu Val Ser Gln Phe Leu Thr Glu Gly
                370                 375                 380

Ile Ile Met Lys Asp Phe Ser His Pro Asn Val Leu Ser Leu Leu Gly
385                 390                 395                 400

Ile Cys Leu Arg Ser Glu Gly Ser Pro Leu Val Val Leu Pro Tyr Met
                405                 410                 415

Lys His Gly Asp Leu Arg Asn Phe Ile Arg Asn Glu Thr His Asn Pro
                420                 425                 430

Thr Val Lys Asp Leu Ile Gly Phe Gly Leu Gln Val Ala Lys Ala Met
                435                 440                 445

Lys Tyr Leu Ala Ser Lys Lys Phe Val His Arg Asp Leu Ala Ala Arg
                450                 455                 460

Asn Cys Met Leu Asp Glu Lys Phe Thr Val Lys Val Ala Asp Phe Gly
465                 470                 475                 480
```

Leu Ala Arg Asp Met Tyr Asp Lys Glu Tyr Tyr Ser Val His Asn Lys
            485                 490                 495
Thr Gly Ala Lys Leu Pro Val Lys Trp Met Ala Leu Glu Ser Leu Gln
        500                 505                 510
Thr Gln Lys Phe Thr Thr Lys Ser Asp Val Trp Ser Phe Gly Val Val
    515                 520                 525
Leu Trp Glu Leu Met Thr Arg Gly Ala Pro Pro Tyr Pro Asp Val Asn
530                 535                 540
Thr Phe Asp Ile Thr Val Tyr Leu Leu Gln Gly Arg Arg Leu Leu Gln
545                 550                 555                 560
Pro Glu Tyr Cys Pro Asp Pro Leu Tyr Glu Val Met Leu Lys Cys Trp
                565                 570                 575
His Pro Lys Ala Glu Met Arg Pro Ser Phe Ser Glu Leu Val Ser Arg
            580                 585                 590
Ile Ser Ala Ile Phe Ser Thr Phe Ile Gly Glu His Tyr Val His Val
        595                 600                 605
Asn Ala Thr Tyr Val Asn Val Lys Cys Val Ala Pro Tyr Pro Ser Leu
    610                 615                 620
Leu Ser Ser Glu Asp Asn Ala Asp Asp Glu Val Asp Thr Arg Pro Ala
625                 630                 635                 640
Ser Phe Trp Glu Thr Ser
            645

<210> SEQ ID NO 19
<211> LENGTH: 689
<212> TYPE: DNA
<213> ORGANISM: Homo sapiens

<400> SEQUENCE: 19

```
agcttcgagc caagcagcgt cctggggagc gcgtcatggc cttaccagtg accgccttgc      60
tcctgccgct ggccttgctg ctccacgccg ccaggccgag ccagttccgg gtgtcgccgc     120
tggatcggac ctggaacctg ggcgagacag tggagctgaa gtgccaggtg ctgctgtcca     180
acccgacgtc gggctgctcg tggctcttcc agccgcgcgg cgccgccgcc agtcccacct     240
tcctcctata cctctcccaa aacaagccca aggcggccga ggggctggac acccagcggt     300
ctcgggcaa gaggttgggg gacaccttcg tcctcaccct gagcgacttc cgccgagaga     360
acgagggcta ctatttctgc tcggccctga gcaactccat catgtacttc agccacttcg     420
tgccggtctt cctgccagcg aagcccacca cgacgccagc gccgcgacca ccaacaccgg     480
cgcccaccat cgcgtcgcag cccctgtccc tgcgcccaga ggcgtgccgg ccagcggcgg     540
ggggcgcagt gcacacgagg gggctggact tcgcctgtga tatctacatc tgggcgccct     600
tggccgggac ttgtgggggtc cttctcctgt cactggttat caccctttac tgcaaccaca     660
ggaaccgaag acgtgtttgc aaatgtccc                                        689
```

<210> SEQ ID NO 20
<211> LENGTH: 218
<212> TYPE: PRT
<213> ORGANISM: Homo sapiens

<400> SEQUENCE: 20

Met Ala Leu Pro Val Thr Ala Leu Leu Leu Pro Leu Ala Leu Leu Leu
1               5                   10                  15
His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
         35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
                180                 185                 190

Cys Gly Val Leu Leu Leu Ser Leu Val Ile Thr Leu Tyr Cys Asn His
            195                 200                 205

Arg Asn Arg Arg Arg Val Cys Lys Cys Pro
210                 215

<210> SEQ ID NO 21
<211> LENGTH: 1289
<212> TYPE: DNA
<213> ORGANISM: Homo sapiens

<400> SEQUENCE: 21

```
cagtgaatta gttcgctacg atgcaagagt acacactcct catttggata ggcttgtaag    60
tgcccgaagt gtaagcccaa ctacagaaat ggtttcaaat gaatctgtag actaccgagc   120
tactttccca gaagatcagt ttcctaattc atctcagaac ggttcatgcc gacaagtgca   180
gtatcctctg acagacatgt cccccatcct aactagtggg gactctgata tatccagtcc   240
attactgcaa aatactgtcc acattgacct cagtgctcta aatccagagc tggtccaggc   300
agtgcagcat gtagtgattg ggcccagtag cctgattgtg catttcaatg aagtcatagg   360
aagagggcat tttggttgtg tatatcatgg gactttgttg acaatgatg caagaaaat    420
tcactgtgct gtgaaatcct tgaacagaat cactgacata ggagaagttt cccaatttct   480
gaccgaggga atcatcatga aagattttag tcatcccaat gtcctctcgc tcctgggaat   540
ctgcctgcga agtgaagggt ctccgctggt ggtcctacca tacatgaaac atggagatct   600
tcgaaatttc attcgaaatg agactcataa tccaactgta aaagatctta ttggctttgg   660
tcttcaagta gccaaagcga tgaaatatct tgcaagcaaa aagtttgtcc acagagactt   720
ggctgcaaga aactgtatgc tggatgaaaa attcacagtc aaggttgctg attttggtct   780
tgccagagac atgtatgata agaatactaa tagtgtacac aacaaaacag gtgcaaagct   840
gccagtgaag tggatggctt tggaaagtct gcaaactcaa aagtttacca ccaagtcaga   900
tgtgtggtcc tttggcgtcg tcctctggga gctgatgaca agaggagccc acccttatcc   960
tgacgtaaac acctttgata taactgttta cttgttgcaa gggagaagac tcctacaacc  1020
```

-continued

```
cgaatactgc ccagacccct tatatgaagt aatgctaaaa tgctggcacc ctaaagccga    1080
aatgcgccca tccttttctg aactggtgtc ccggatatca gcgatcttct ctactttcat    1140
tggggagcac tatgtccatg tgaacgctac ttatgtgaac gtaaaatgtg tcgctccgta    1200
tccttctctg ttgtcatcag aagataacgc tgatgatgag gtggacacac gaccagcctc    1260
cttctgggag acatcatagt gctagtact                                      1289
```

<210> SEQ ID NO 22
<211> LENGTH: 425
<212> TYPE: PRT
<213> ORGANISM: Homo sapiens

<400> SEQUENCE: 22

```
Ser Glu Leu Val Arg Tyr Asp Ala Arg Val His Thr Pro His Leu Asp
1               5                   10                  15

Arg Leu Val Ser Ala Arg Ser Val Ser Pro Thr Thr Glu Met Val Ser
            20                  25                  30

Asn Glu Ser Val Asp Tyr Arg Ala Thr Phe Pro Glu Asp Gln Phe Pro
        35                  40                  45

Asn Ser Ser Gln Asn Gly Ser Cys Arg Gln Val Gln Tyr Pro Leu Thr
    50                  55                  60

Asp Met Ser Pro Ile Leu Thr Ser Gly Asp Ser Asp Ile Ser Ser Pro
65                  70                  75                  80

Leu Leu Gln Asn Thr Val His Ile Asp Leu Ser Ala Leu Asn Pro Glu
                85                  90                  95

Leu Val Gln Ala Val Gln His Val Val Ile Gly Pro Ser Ser Leu Ile
            100                 105                 110

Val His Phe Asn Glu Val Ile Gly Arg Gly His Phe Gly Cys Val Tyr
        115                 120                 125

His Gly Thr Leu Leu Asp Asn Asp Gly Lys Lys Ile His Cys Ala Val
    130                 135                 140

Lys Ser Leu Asn Arg Ile Thr Asp Ile Gly Glu Val Ser Gln Phe Leu
145                 150                 155                 160

Thr Glu Gly Ile Ile Met Lys Asp Phe Ser His Pro Asn Val Leu Ser
                165                 170                 175

Leu Leu Gly Ile Cys Leu Arg Ser Glu Gly Ser Pro Leu Val Val Leu
            180                 185                 190

Pro Tyr Met Lys His Gly Asp Leu Arg Asn Phe Ile Arg Asn Glu Thr
        195                 200                 205

His Asn Pro Thr Val Lys Asp Leu Ile Gly Phe Gly Leu Gln Val Ala
    210                 215                 220

Lys Ala Met Lys Tyr Leu Ala Ser Lys Lys Phe Val His Arg Asp Leu
225                 230                 235                 240

Ala Ala Arg Asn Cys Met Leu Asp Glu Lys Phe Thr Val Lys Val Ala
                245                 250                 255

Asp Phe Gly Leu Ala Arg Asp Met Tyr Asp Lys Glu Tyr Tyr Ser Val
            260                 265                 270

His Asn Lys Thr Gly Ala Lys Leu Pro Val Lys Trp Met Ala Leu Glu
        275                 280                 285

Ser Leu Gln Thr Gln Lys Phe Thr Thr Lys Ser Asp Val Trp Ser Phe
    290                 295                 300

Gly Val Val Leu Trp Glu Leu Met Thr Arg Gly Ala Pro Pro Tyr Pro
305                 310                 315                 320

Asp Val Asn Thr Phe Asp Ile Thr Val Tyr Leu Leu Gln Gly Arg Arg
```

-continued

```
                    325                 330                 335
Leu Leu Gln Pro Glu Tyr Cys Pro Asp Pro Leu Tyr Glu Val Met Leu
            340                 345                 350

Lys Cys Trp His Pro Lys Ala Glu Met Arg Pro Ser Phe Ser Glu Leu
            355                 360                 365

Val Ser Arg Ile Ser Ala Ile Phe Ser Thr Phe Ile Gly Glu His Tyr
        370                 375                 380

Val His Val Asn Ala Thr Tyr Val Asn Val Lys Cys Val Ala Pro Tyr
385                 390                 395                 400

Pro Ser Leu Leu Ser Ser Glu Asp Asn Ala Asp Asp Glu Val Asp Thr
            405                 410                 415

Arg Pro Ala Ser Phe Trp Glu Thr Ser
            420                 425

<210> SEQ ID NO 23
<211> LENGTH: 8
<212> TYPE: DNA
<213> ORGANISM: Homo sapiens

<400> SEQUENCE: 23 ggatccgg                                                        8
```

TRANSGENIC NON-HUMAN MAMMALS EXPRESSING CONSTITUTIVELY ACTIVATED TYROSINE KINASE RECEPTORS

This invention claims priority from provisional U.S. application Ser. No. 60/360,889 filed Mar. 1, 2002, which is incorporated herein by reference in its entirety.

FIELD OF THE INVENTION

The invention is directed toward tumor-susceptible transgenic non-human mammals. The invention further pertains to the use of such mammals in the development of anticancer agents and therapies.

BACKGROUND OF THE INVENTION

Recent advances in recombinant DNA and genetic techniques have made it possible to introduce and express a desired sequence or gene in a recipient animal. Through the use of such methods, animals have been engineered to carry non-naturally occurring sequences or genes, that is, sequences or genes that are not normally or naturally present in the unaltered animal. The techniques have also been used to produce animals which exhibit altered expression of naturally present sequences or genes.

Animals produced through the use of these methods can be either "chimeric", in which only some of the animal's cells contain and express the introduced sequence or gene, or "transgenic", in which all of the cells of the animal contain the introduced sequence or gene. Consequently, in the case of transgenic animals every animal is capable of transmitting the introduced genetic material to its progeny as compared to the chimeric animals in which transmittal to progeny is dependent upon whether the introduced material is present in the germ cells of the animal.

The high efficiency transformation of cultured mammalian cells has been accomplished by direct microinjection of specific DNA sequences into the cell nucleus (Capecchi, M., *Cell* 22:479-488 (1980)). More specifically, it has also been demonstrated that DNA could be microinjected into mouse embryos and found in the resultant offspring (Gordon et al., *P.N.A.S. U.S.A.* 77:7380-7384 (1978)). Thus, the ability to produce certain transgenic mice is described and well known.

The basic procedure for producing transgenic mice requires the recovery of fertilized eggs from newly mated female mice and then microinjecting into the male pronucleus of said egg the DNA that contains the sequence or gene to be transferred into the mouse. The microinjected eggs are then implanted in the oviducts of one-day pseudopregnant foster mothers and allowed to proceed to term. The newborn mice are then tested for the presence of the microinjected DNA by means known in the art and appropriate to detect the presence of the microinjected DNA. See, for example, Wagner et al. *P.N.A.S. U.S.A.* 78:6376-6380 (1981), U.S. Pat. No. 4,873,191, which describes the production of mice capable of expressing rabbit beta-globin in its erythrocytes.

The insulin-like growth factor I receptor (referred to as "IGF-1R" or "IGF1R") is a transmembrane tyrosine kinase which is overexpressed or activated in many human cancers including colon, breast, lung, prostate, glioblastoma and melanoma. IGF1R is thought to be required for the establishment and maintenance of the transformed phenotype and to exert an anti-apoptotic effect in tumorigenesis. Baserga, R., *Cancer Research* 55:249-252 (1995). Activation of the receptor is initiated by the binding of either IGF-I or IGF-II to the two α-subunits of the IGF1R, i.e., receptor dimerization, resulting in the autophosphorylation of critical tyrosine residues in the catalytic domain of the β-subunit. Kato et al., *J. Biol. Chem.* 265:2655-2661 (1993); Gronborg et al., *J. Biol. Chem.* 258:23435-23440 (1993). Ligand binding also leads to phosphorylation and subsequent activation of downstream substrates thought to be involved in growth regulation and differentiation. Ottensmeyer et al., *Biochemistry* 39:12103-12112 (2000). In vitro models have been developed to study the role of kinase dimerization in the activation of the IGF1R that utilize fusion proteins comprising the soluble kinase domain of IGF1R and the homodimeric glutathione S-transferase (GST), Baer et al., *Biochemistry* 40:14268-14278 (2001).

To date, the transgenic models established for studying IGF1R signaling have been limited to overexpression of the ligands for IGF1 R (Bol et al., *Oncogene* 14:1725-1734 (1997); DiGiovanni et al., *Cancer Research* 60:1561-1570 (2000)). These models are further complicated by the existence of a family of IGF binding proteins (IGFBPs), which serve to modulate the bioavailability of free IGF-I and IGF-II, resulting in a long latent period for tumor development.

One approach to studying in vitro the constitutive stimulation of a receptor in the absence of ligand binding activation has utilized a chimeric oncogenic receptor-type tyrosine kinase comprising the extracellular and transmembrane domains of CD8 with the kinase domain of c-Eyk (Zong et al., *EMBO Journal,* Vol.15, No. 17, 4516-4525 (1996)). The resulting chimera showed elevated kinase activity and caused cellular transformation. Such chimeric receptors may incorporate the extracellular, transmembrane and cytoplasmic domains from the same or different species. The preparation and use of chimeric receptors comprising cytokines and other kinase domains are known in the art. See, for example, Lawson et al., WO 99/57268; M. Roberts, U.S. Pat. No. 5,712,149; and Capon et al., U.S. Pat. No. 5,741,899.

It is therefore of interest to develop a transgenic non-human mammalian model for ligand-independent IGF-1 receptor-driven tumorigenesis. It is also desirable that the animal develops tumors that overexpress IGF1R within a fairly short period of time from birth, facilitating the analysis of multigenerational pedigrees. Such a model can be used to study the pathogenesis and treatment of tumors overexpressing or having activated IGF1R. The instant invention represents such a model using a chimeric receptor.

SUMMARY OF THE INVENTION

The invention is directed to a transgenic non-human mammal whose germ cells and somatic cells express a constitutively activated tyrosine kinase receptor that acts as an oncogene sequence. The constitutive activation of the tyrosine kinase receptor results from a transgene comprising a dimerizable-inducing moiety and the catalytic kinase domain of the tyrosine kinase receptor to be activated. In a preferred embodiment of the invention, the non-human mammal is a mouse, the transgene comprises the extracellular and transmembrane domains of CD8 and the intracellular catalytic kinase domain of IGF1R, and the constructively activated tyrosine kinase receptor is that of IGF1R. The invention further comprises mammalian embryos carrying the constructively activated tyrosine kinase receptor capable of developing into viable transgenic animals whose progeny carry the constructively activated tyrosine kinase receptor after breeding forward by sexual reproduction. The invention further comprises DNA constructs comprising a selected promoter plus the constructively activated tyrosine kinase receptor cDNA or DNA segments cloned into plasmids for ultimate insertion into the genome of a mammal.

The transgenic non-human mammals of the invention are characterized by specificity for the constructively activated tyrosine kinase receptor that is expressed by the transgenic non-human mammal. In a preferred embodiment of the invention, the transgenic mice express constructively active IGF1R which drives tumorigenesis; adenocarcinomas develop in the salivary and mammary glands of the transformed mice as early as eight weeks of age. Tumors from the transgenic mice that express the transgene when grafted into nude mice are sensitive to inhibitors of the specific constructively activated tyrosine kinase receptor, but not other tyrosine kinase receptors, and are thus capable of being utilized as tools for the identification and optimization of molecules and chemical entities for novel anticancer therapies. Thus, the invention also embodies non-human mammals and methods for the identification of selective modulators of constructively activated tyrosine kinase receptors and pharmaceutical compositions comprising the selective modulators so identified.

Thus, the invention provides a transgenic non-human mammal whose somatic and germ line cells contain a genome comprised of a transgene encoding a sequence for a constructively activated tyrosine kinase receptor, wherein the non-human mammal is more susceptible to developing tumors specific to the constructively activated tyrosine kinase receptor.

The invention also provides a transgenic non-human mammal which expresses a genomic DNA fragment which comprises a coding sequence for a constructively activated tyrosine kinase receptor, wherein said transgenic non-human mammal can be bred to produce progeny non-human mammals whose genomes comprise said genomic DNA fragment.

The invention further provides a method for obtaining a target mouse whose genome comprises a genomic DNA fragment wherein the DNA fragment comprises a coding sequence for a constructively activated tyrosine kinase receptor, wherein said mouse can be bred to produce progeny mice whose genomes comprise said genomic DNA fragment, said method comprising the steps of:
  (a) isolating a fertilized egg from a first female mouse;
  (b) transferring a genomic DNA fragment which comprises a coding sequence for a constructively activated tyrosine kinase receptor into said fertilized egg;
  (c) transferring said fertilized egg containing said genomic DNA fragment to the uterus of a pseudopregnant second female mouse; and
  (d) maintaining said second female mouse such that:
    (i) said second female mouse becomes pregnant with an embryo derived from said fertilized egg containing said genomic DNA fragment;
    (ii) said embryo develops into said target mouse; and
    (iii) said target mouse is viably born from said second female mouse;

wherein the genome of said target mouse comprises said genomic DNA fragment and wherein said mouse can be bred to produce progeny mice whose genomes comprise said genomic DNA fragment.

The invention also includes a method of screening for selective modulators of a constructively activated tyrosine kinase receptor for use in treating cancer resulting from a constructively activated tyrosine kinase receptor which comprises administering an investigational substance to a non-human mammal of the invention and assaying the cancer treating efficacy of said investigational substance in said cancer. Also provided is a pharmaceutical composition for treating cancer resulting from a constitutitively activated tyrosine kinase receptor which comprises a substance determined by this method of screening for selective modulators to have cancer treating efficacy in said cancer.

The invention further includes a method for producing a transgenic mouse that develops tumors specific for a constructively activated tyrosine kinase receptor comprising the steps of: (a) obtaining a tumor fragment from a transgenic non-human animal of the invention that is a mouse; (b) implanting subcutaneously said tumor fragment to a recipient nude mouse; and (c) maintaining said mouse from step (b) under conditions to promote growth of said mouse and said tumor.

Yet another aspect of the invention is a method for producing a transgenic mouse cell line that expresses a constructively activated tyrosine kinase receptor comprising the steps of: (a) obtaining a tumor fragment from a transgenic non-human animal of the invention that is a mouse; (b) isolating cells from said tumor sample; and (c) placing the isolated cells under such conditions as to maintain growth and viability of said isolated cells.

BRIEF DESCRIPTION OF THE DRAWINGS

FIGS. 1A and 1B are diagrammatic representations of the dimerized MMTV-CD8:IGF1R (MCI) construct. The cross hatched portion of the diagram represents the CD8 extracellular and transmembrane domains and the open portion of the diagram represents the intracellular, catalytic kinase domain of IGF1R.

FIG. 8A shows representative xenografted salivary tumors from transgenic line MCI-19 and FIG. 8B shows representative mammary tumors from transgenic line MCI-15.

FIG. 11A is a representative photograph of primary cells established on poly-D lysine matrix in monolayer. FIG. 11B is a representative graph of the exponential growth of cells in media.

DETAILED DESCRIPTION OF THE INVENTION

Figure 2:
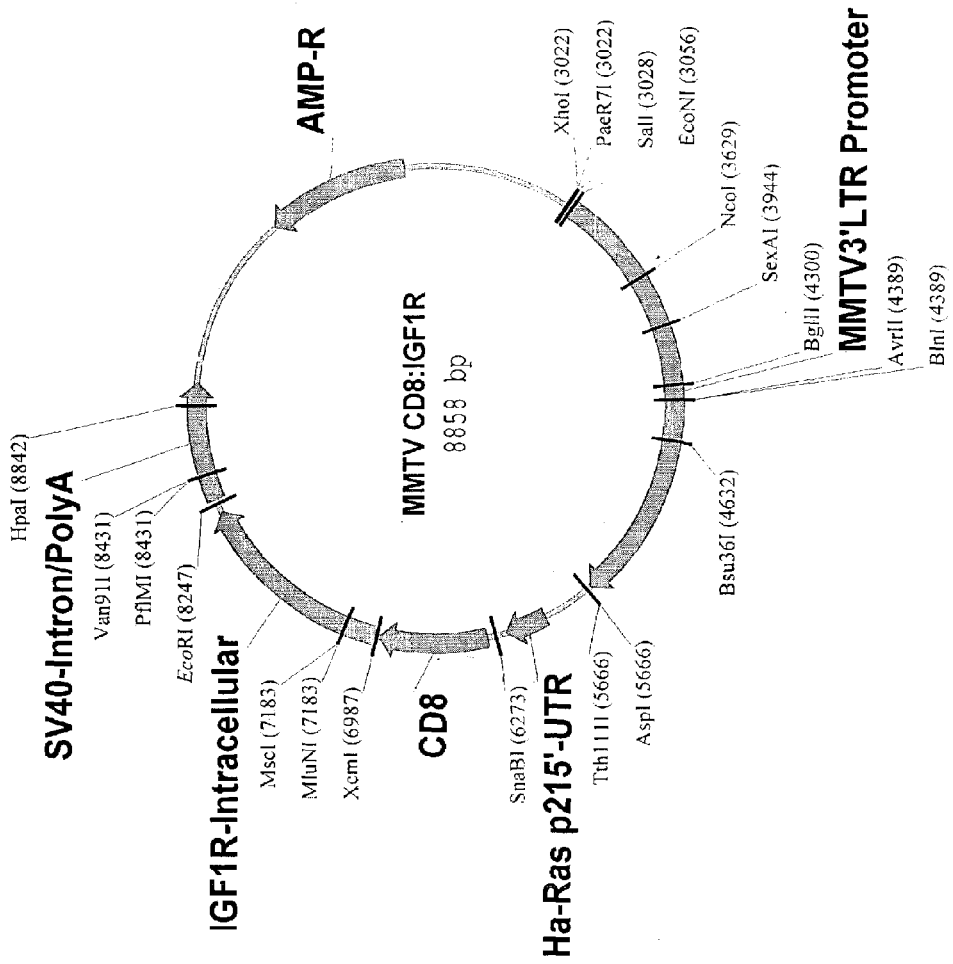
FIG. 2 is a diagrammatic representation of the MMTV-CD8:IGF1R (MCI) construct. The CD8:IGF1R fusion gene was cloned into a vector in such a way that it was downstream of a MMTV promoter and was flanked with intron and polyA sequences for efficient message processing

Cancer in humans develops through a multi-step process, indicating that multiple changes must occur to convert a normal cell into one with a malignant phenotype. One class of involved genes includes cellular oncogenes which, when activated by mutation or when expressed inappropriately, override normal cellular control mechanisms and promote unbridled cell proliferation.

The invention relates to production of transgenic non-human mammals containing within their genomes a chimeric receptor that when expressed results in the constitutive activation of a tyrosine kinase and the development of tumors early in age. The tumors have been found to express high levels of the activated tyrosine kinase, which in turn can be transplanted into nude mice as xenografts. The tumors so generated have been used to establish cell lines for use in biological studies.

The invention also relates to a transgenic non-human mammal whose somatic and germ line cells contain a genome comprised of a transgene encoding a sequence for a constructively activated tyrosine kinase receptor, wherein the non-human mammal is more susceptible to developing tumors specific to the constructively activated tyrosine kinase receptor.

In a preferred embodiment, described in the examples that follow, the construct is the engineered human CD8:IGF1R fusion gene. Those skilled in the art will recognize that other constructs can be generated that will produce similar results, that is, that will lead to the dimerization and constitutive activation of the tyrosine kinase receptor from which the cytoplasmic catalytic kinase domain has been engineered. By way of example, and not intending to be limited thereto, the transgene of the invention may comprise a dimerization-inducible moiety, such as CD8 or glutathione S-transferase (GST), and an intracellular kinase domain selected from the group of receptors with tyrosine kinase activity including, but not limited to, epidermal growth factor receptor (EGFR), HER2, insulin receptor (IR), insulin-like growth factor (IGF1R), platelet-derived growth factor (PDGFR), fibroblast growth factor (FGFR) and hepatocyte growth factor receptor (Met).

The nucleotide sequences (human cDNA) used herein were cloned using standard molecular biology techniques (Maniatus et al., *Molecular Cloning: A Laboratory Manual*, Cold Spring Harbor Laboratory (1982); Ausubel, F. M. et al., *Current Protocols in Molecular Biology,* John Wiley and Sons, Volume 2 (1991)) based on sequences available in the public domain (GenBank). Nucleotide sequences from other mammals can be employed in the invention herein, provided that membrane associated dimerization causes constitutive activation of the tyrosine kinase receptor, that is, said activity results in signal transduction in the mammalian cells. In the invention, expression of the transgene results in the dimerization of the tyrosine kinase receptor to which the fusion protein binds and in turns results in the constitutive activation of the receptor in the absence of the naturally occurring ligand binding.

The construct may also comprise selected nucleic acid regions associated with the transgene (as by fusion therewith) for mediation of, for example, its introduction into the target genome, its expression loci in the transgenic mammal, on/off external regulation of transgene expression, and other desired features, as generally known in the art.

In one aspect, the invention provides transgenic lines that express activated IGF1R under the control of the mouse mammary tumor virus (MMTV) promoter. Several lines of mice were generated that expressed the transgene in both the salivary and mammary glands; mice harboring the transgene developed adenocarcinomas in these tissues as early as eight weeks of age. In culture, cell lines derived from salivary tumors are sensitive to inhibitors of the IGF1R, but are significantly less sensitive to inhibitors specific for other receptors, such as the EGF receptor. Importantly, when grafted into nude mice, these lines form tumors that grow well and are sensitive to standard cytotoxic agents. The transgenic animals described herein may serve as efficient tools in the identification, development, and optimization of biological and chemical moieties for use as anticancer therapies directed at inhibition of the IGF-1 receptor.

In accordance with the invention, a construct was generated in which the extracellular and transmembrane domains of the human CD8 antigen (Sukhatmet et al., *Cell* 40(30): 591-597 (1985)) were fused to the intracellular, catalytic tyrosine kinase domain of IGF1R (FIG. 1A). This fusion protein alleviates the necessity for IGF ligand to cause dimerization of the IGF1R and subsequent autophosphorylation. Instead, the CD8 portion of the fusion protein dimerizes in a ligand-independent way, resulting in constitutive activation of the tyrosine kinase (FIG. 1B). By constitutive activation it is meant dimerization of the fusion protein, as driven by the CD8 domain, which results in autophosphorylation of the kinase domain, a property needed for intracellular signal transduction.

The engineered human CD8:IGF1R fusion gene was cloned into a vector in such a way that it was downstream of a mouse mammary tumor virus (MMTV) promoter and was flanked with intron and polyA sequences for efficient message processing. The MMTV promoter, when expressed in vivo in the animal, drives transcription of downstream sequences in the mammary and salivary glands of mice. One skilled in the art would be able to clone the transgene of the invention into a vector under the control of other promoters that drive tumor development in the skin of the non-human mammal. For example, the human CD8:IGF1R transgene was cloned into a vector under the control of the K14 promoter with similar results.

FIG. 2 provides a diagrammatic representation of the MMTV-CD8:IGF1R transgene construct. The sequence of this transgene construct is provided in SEQ ID NO:1 and a plasmid of this construct was deposited with the American Type Culture Collection ("ATCC"), 10801 University Boulevard, Manassas, Va. 20110-2209, on Jan. 10, 2003 and has been given ATCC Deposit Designation PTA-4930. The deposit referred to herein will be maintained under the terms of the Budapest Treaty on the International Recognition of the Deposit of Micro-Organisms for purposes of Patent Procedure. These deposits are provided merely as convenience to those of skill in the art and are not an admission that a deposit is required under 35 U.S.C. §112. The sequence(s) of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

Figure 3:
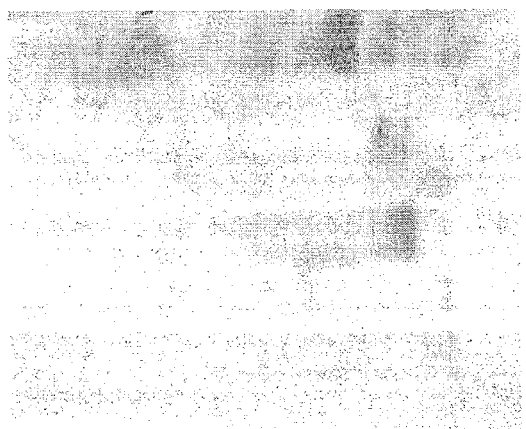
FIG. 3 shows a representative Northern blot analysis of the salivary tissue of a control and five progeny mice found to have passed the transgene (CD8:IGF1R). Each lane contains 20 μg of total RNA isolated from salivary gland tissue resolved on a 1% agarose gel in 17.5% formaldehyde.
Figure 4:
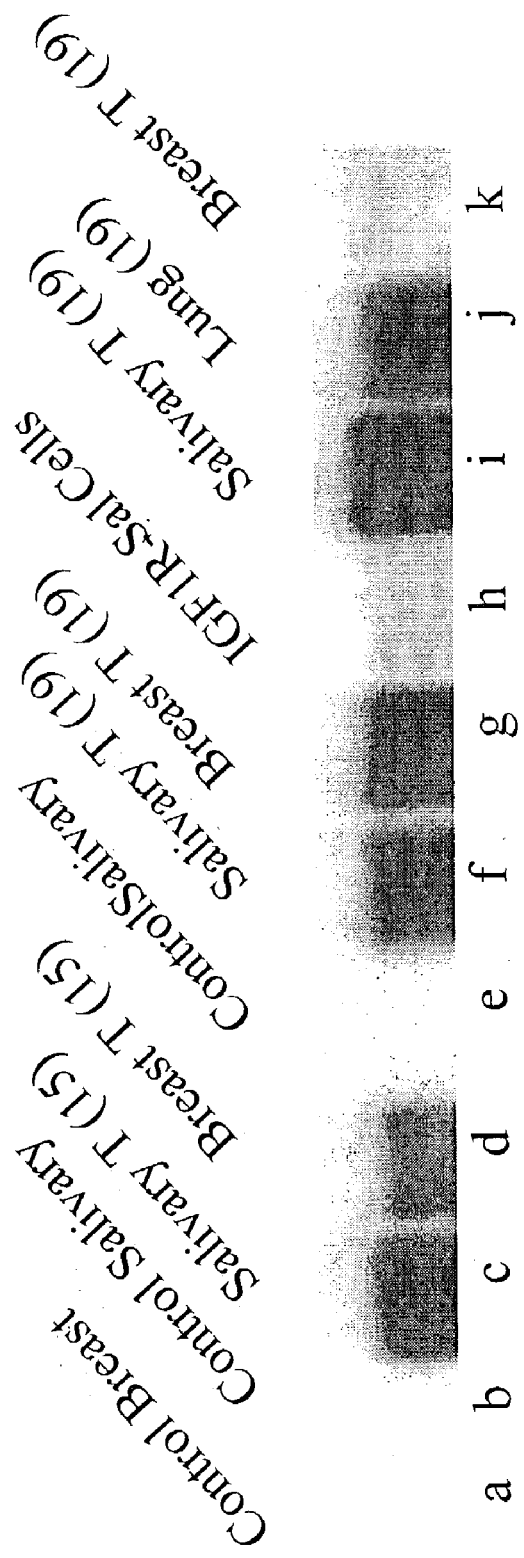
FIG. 4 shows a representative Northern blot analysis of control and tumored salivary mammary tissue showing expression of the transgene. Lane a—control mammary tissue; lane b—control salivary tissue; lane c—salivary tissue (line 15); lane d—mammary tissue (line 15); lane e—control salivary tissue; lane f—salivary tissue (line 19); lane g—mammary tissue (line 19); lane h—IGF1R-Sal Cells; lane i—xenografted salivary tissue (line 19); lane j—xenografted lung tissue (line 19); and xenografted mammary tissue (line 19). For each sample polyA mRNA was isolated from 50 μg of total RNA by the methods described in Example 4 below. The isolated mRNA was resolved on a 1% agarose gel in 17.5% formaldehyde.

Microinjection of the MMTV-CD8:IGF1R construct of SEQ ID NO:1 into the pronucleus of fertilized oocytes resulted in the generation of eight founder mice carrying the transgene (CD8:IGF1R) DNA. Of these eight mice, six were bred to produce progeny and five were found to pass the transgene in a Mendelian fashion to offspring. Mice from these five lines were subsequently examined for expression of the transgene in salivary gland tissue. As can be seen in FIG. 3, one transgenic mouse line, identified as MCI-19, had particularly high levels of transgene expression in the salivary glands. Subsequently, another transgenic mouse line, identified as MCI-15, was also shown to have high levels of salivary gland expression (data not shown). Two transgenic mouse lines developed tumors of the salivary and mammary glands (lines MCI-15 and MCI-19) and were retained for further studies. Tumors from both salivary gland and mammary gland tumors were also shown to have high levels of expression of the transgene, as did xenografted tumors and cell lines, as compared to tissues from non-transgenic mice which showed no expression of the transgene (FIG. 4)

Figure 5B:
FIGS. 5A (mammary) and 5B (salivary) show the transgenic mouse (line MCI-19) with representative multifocal mammary tumors.
Figure 5A:
Figure 6:
FIG. 6 shows representative normal (right lung) and lung metastases (left lung) of representative salivary gland tumors.

Both male and female mice from each transgenic line developed tumors. Female mice began to develop tumors in the salivary gland at about 90 days of age, although enlarged glands are obvious just after weaning. Once tumors fully develop, they grow rapidly such that mice are often euthanized within a few weeks of the initial observation of the tumor. Mammary tumor development, however, is more latent, often not occurring until the animals are about 150 days of age or older. Tumors in the mammary tissue are often multifocal, arising simultaneously in multiple regions of the gland with no apparent bias for location (FIGS. 5A (mammary) and 5B (salivary)). In male mice, salivary glands develop with the same frequency as in females and within the same time frame. Mammary gland tumors have also been observed in a few male mice, although with reduced incidence compared to females. Interestingly, metastasis of the salivary gland tumors to the lungs has been observed in both male and female mice (FIG. 6). Because of the rapid growth rate of the tumors in the salivary gland, surgical removal of the affected gland is often required to allow the animal to survive long enough to develop substantial metastasis.

Figure 7:
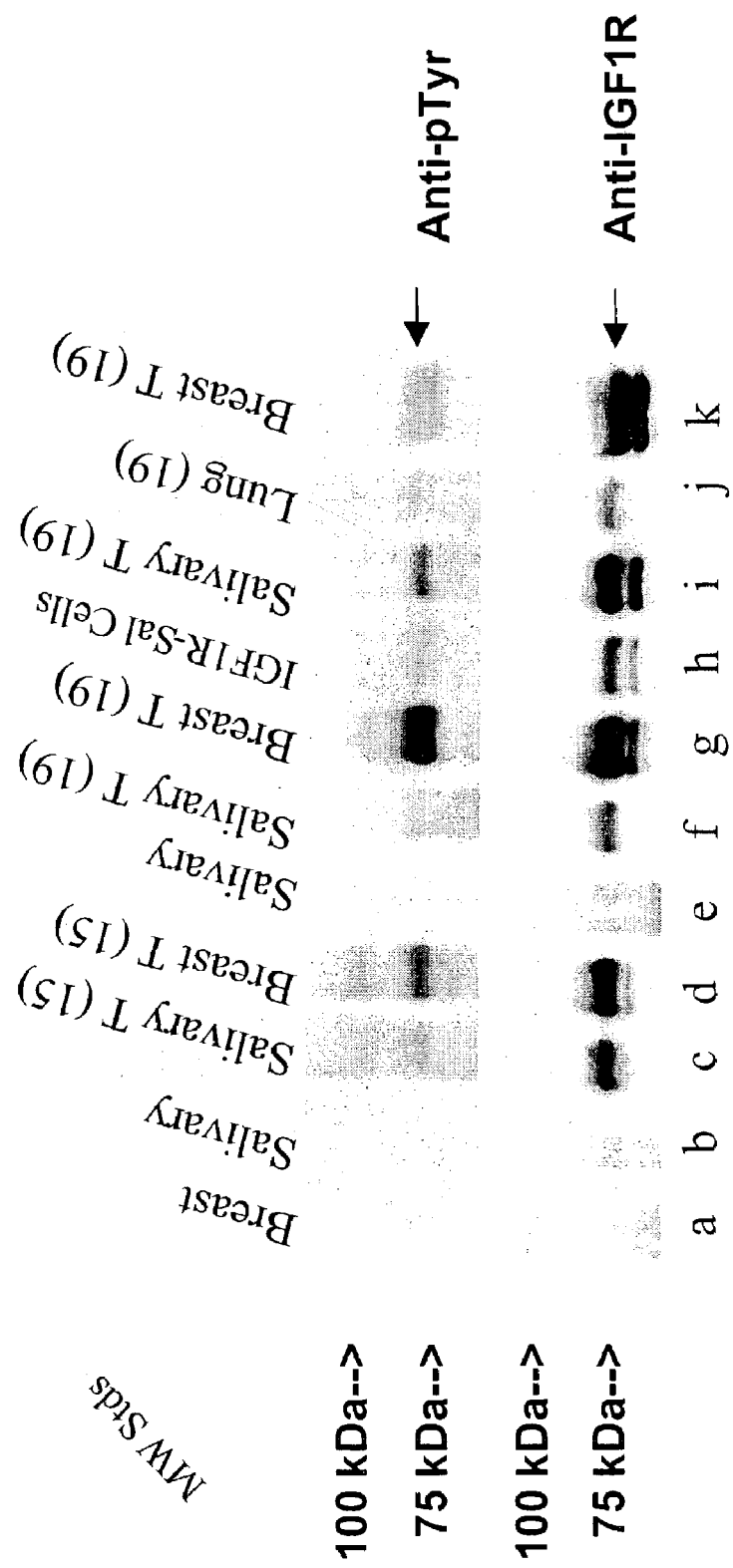
FIG. 7 shows representative Western blot analysis of salivary and mammary tissue from normal and tumored mice. Lane a—normal mammary tissue; lane b—normal salivary tissue; lane c—salivary tissue (line 15); lane d—mammary tissue (line 15); lane e—normal salivary tissue; lane f—salivary tissue (line 19); lane g—mammary tissue (line 19); lane h—IGF1R-Sal cells; lane i—xenografted salivary tissue (line 19); lane j—xenografted lung tissue (line 19); and lane k—xenografted mammary tissue (line 19).

In an effort to demonstrate the causal relationship between the oncogene activity of the transgene and tumorigenesis, activity of IGF1R kinase was assessed in a number of samples (FIG. 7). Using antibodies to the CD8 portion of the fusion protein, CD8:IGF1R proteins were immunoprecipitated from lysates of tissue samples, tumors, and cell lines as described in the examples that follow. Resolution of this immunoprectipitate on polyacrylamide gels and subsequent immunoblotting with antiphosphotyrosine antibodies enabled observation of the level of activation of the CD8:IGF1R fusion protein in these samples. As shown in FIG. 7, there is significant phosporylation of the IGF1R tyrosine kinase in the tumor samples from both transgenic lines, MCI-15 and MCI-19, the xenografted tumors, and the IGF1R-Sal cell line, but not in tissues from the control, i.e., non-transgenic mice.

Figure 9:
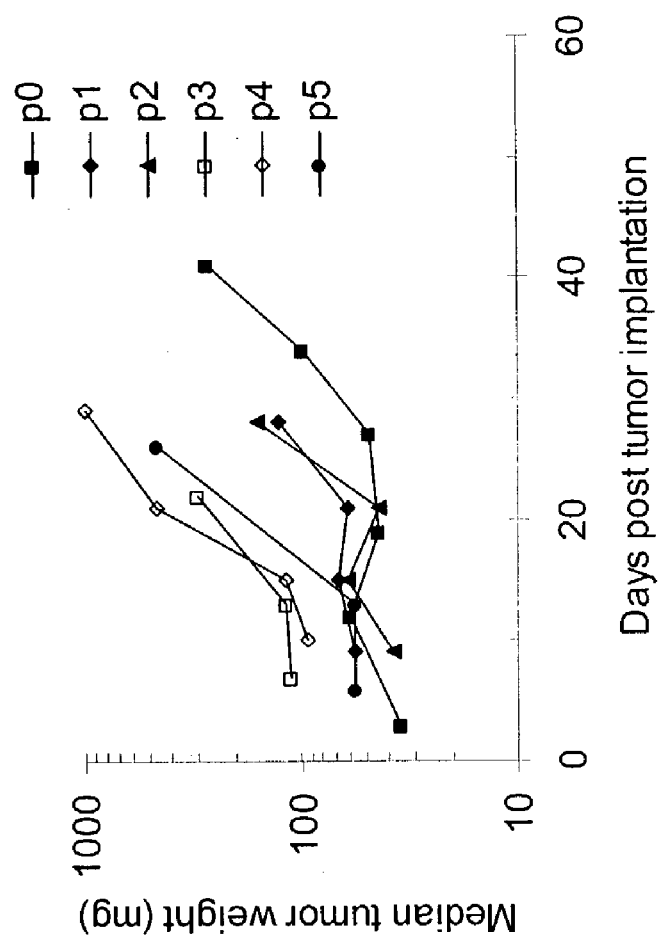
FIG. 9 shows representative in vivo growth of IGF1R-Sal tumors from transgenic line MCI-19 implanted subcutaneously into nude mice at various points of time following implantation.
Figure 10:
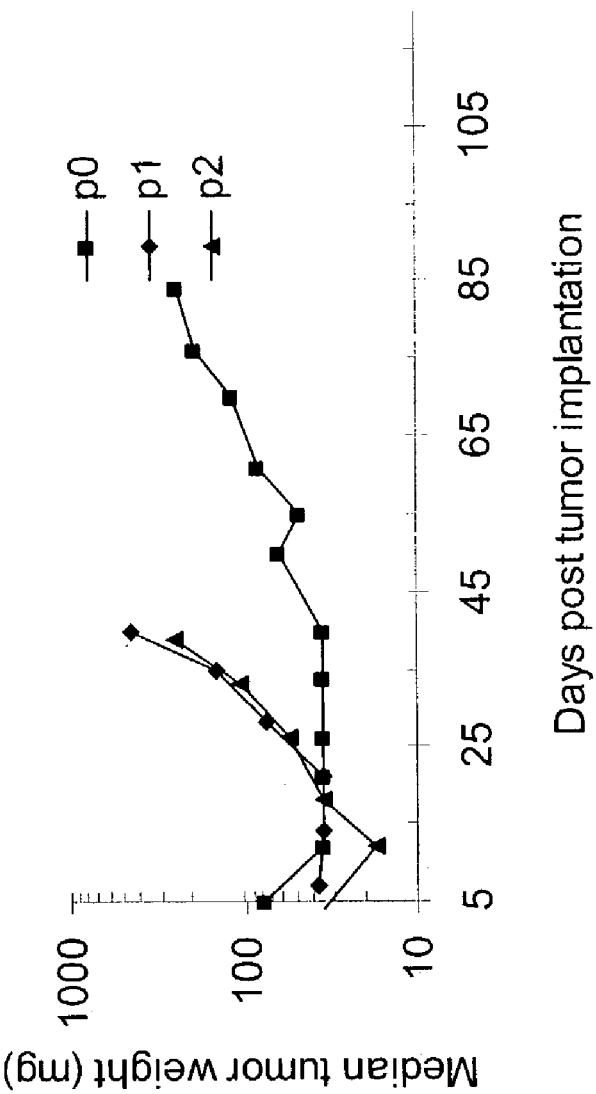
FIG. 10 shows representative in vivo growth of IGF1R-Mam tumors from transgenic line MCI-15 implanted subcutaneously into nude mice at various points of time following implantation.

In order to determine the tumorigenic potential of these lesions observed in the transgenic mice, tumors from both salivary and mammary glands of MCI mice were transferred to nude (nu/nu) mice. Fragments from both tumor types grew when implanted subcutaneously on the ventral side of nude mice within a few weeks. Both mammary gland tumors from MCI-15 and salivary gland tumors from MCI-19 grew as xenografts (FIGS. 8A and 8B). FIG. 9 shows representative in vivo growth of IGF1R-Sal tumors from transgenic line MCI-19 implanted subcutaneously into nude mice at various points of time following implantation. In the early passages of the tumor, the tumors grew slowly and inconsistently, with roughly 20% showing no growth. With increasing passages, the rate of tumor growth improved and tumor take-rates became 100% by the third sequential transfer of tumors from mouse to mouse (passage 3). FIG. 10 shows representative in vivo growth of IGF1R-Mam tumors from transgenic line MCI-15 implanted subcutaneously into nude mice at various points of time following implantation. The growth of the initial passage (p0, from transgenic mouse host to nude mice) was slow with a significant percentage rated as no-take (33%). In subsequent passages both the growth and take-rate improved.

Figure 11B:
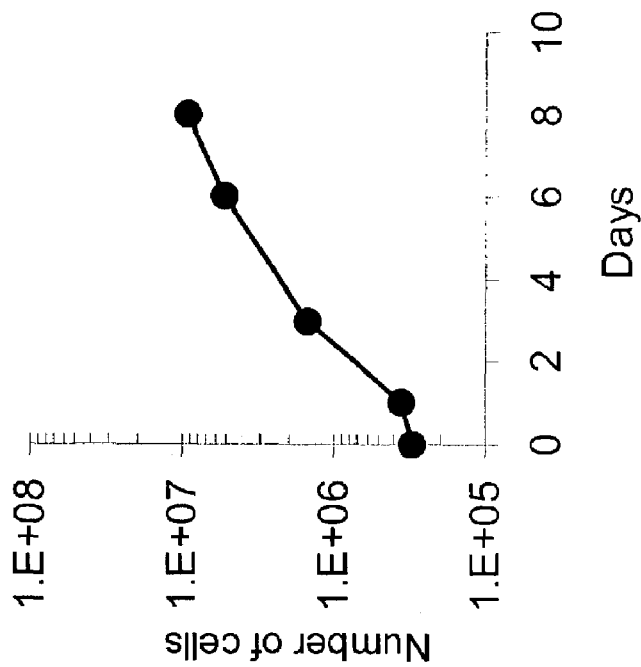
FIGS. 11A and 11B show representative in vitro growth of the IGF1R-Sal cell line.
Figure 11A:
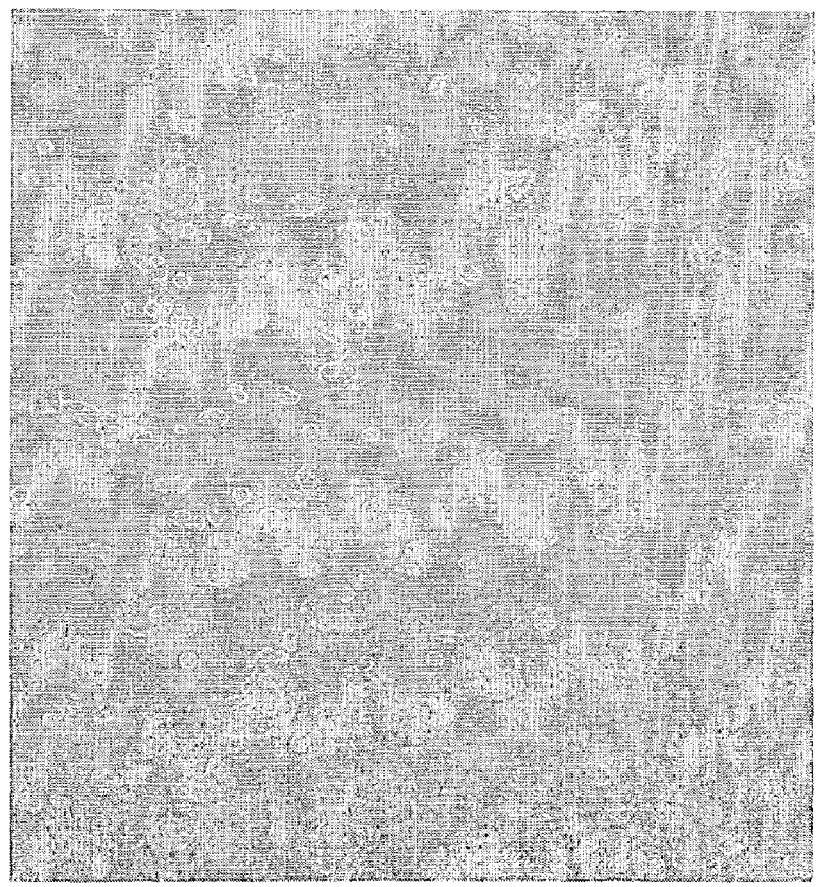

An in vitro cell line was established from the IGF1R-Sal tumors grown in nude mice. Tumor cells isolated from tumor xenografts and seeded onto tissue culture dishes coated with various extracellular matrices behaved and grew very differently. Collagens I and IV, fibrocectin and laminin all appeared to facilitate and enhance the growth of fibroblasts. Poly-D-lysine coated dishes were found to provide the optimal condition for IGF1R-Sal cells. In this condition, a continuous IGF1R-Sal cell line was established (FIGS. 11A and 11B) which grows in exponential fashion. The following cell culture condition were utilized: Complete RPMI 1640 media supplemented with 10% fetal bovine serum and 25 mM HEPES.

The transgenic non-human mammals produced herein, the xenografted tumors, and the cell line established therefrom provide useful tools for reiterative cycles of drug evaluation to develop and optimize properties of useful therapies for cancer.

In a specific embodiment described in the examples that follow, the transgenic mouse so produced is an excellent model for studying specifically the role of IGF1R in tumorigenesis and the identification and development of modulators to affect tumorigenesis. In a particular embodiment of the invention, as exemplified below, a transgenic non-human mammal is engineered to express a constructively activated tyrosine kinase receptor. In this particular embodiment, expression of the transgene leads to constructively activated IGF1R without the need for expression of its corresponding ligand and ligand binding. This model is particularly useful in that the tumors produced in these mice are specific to IGF1R. The tumors generated in the mice described herein are exquisitely sensitive to modulators, and more specifically inhibitors, of the engineered kinase domain from which they were generated, while they have limited susceptibility to modulators of other tyrosine kinase receptors. For example, in culture, cell lines derived from tumor cells from the CD8:IGF1R fusion transgenics are sensitive to inhibitors of IGF1R, but are significantly less sensitive to inhibitors specific to EGFR (data not shown). By use of the invention herein, models can be developed that are specific for a particular tyrosine kinase receptor and thus enable the identification and development of selective tyrosine kinase receptor inhibitors.

The transgenic animals of the invention are accordingly useful inter alia for the development of pharmacotherapies for the treatment of cancer, particularly those characterized by the expression of tyrosine kinase receptors. In a preferred embodiment of the invention, the transgenic animals are useful for the identification of selective modulators of constructively activated tyrosine kinase receptors. In a particularly preferred embodiment, the transgenic animals of the invention are useful for the development of pharmaceuticals and therapies for cancers in which IGF1R is overexpressed or activated. Such cancers include, but are not limited to, breast, colon, prostate, and lung cancer.

The invention also provides a method of screening for selective modulators of a constructively activated tyrosine kinase receptor for use in treating cancer resulting from a constructively activated tyrosine kinase receptor. Methods of screening for modulators using transgenic mice are generally known in the art. See, for example, Omer et al., Cancer Research 60, 2680-2688, May 15, 2000. In one aspect, the method of the invention of screening for selective modulators includes the following steps. Tumors that are derived from transgenic mice are excised and implanted in nude mice. Once tumors reach a size of 100 to 200 mm$^3$, mice are randomized into treatment groups for evaluation of investigational substances or compounds that have demonstrated the desired cell potency and pharmacokinetic properties. Compounds are formulated in a vehicle such as 40% PEG400/0.1% Tween 80, and are administered by oral gavage once or twice daily. Tumor volume in animals treated with vehicle alone or with different doses of compounds is measured twice a week. Inhibition of tumor growth is calculated as % T/C, were T and C are, respectively, tumor volumes in animals treated with compounds and control animals treated with vehicle alone. Compounds that showed % T/C of 50% or less at more than one dose below the maximum tolerated dose are considered efficacious.

The invention is further useful for imparting traits accompanying expression of the constructively activated tyrosine kinase receptors into a line or breed of non-human mammals by genetically engineering one or more mammals of the line according to the invention to obtain transgenic mammals carrying at least one transgene in each of their genomes which, when expressed, constructively activates the specific tyrosine kinase receptor from which it was engineered, preferably in the salivary and mammary glands. Transgenic product mammals are then selected for based on the genotyping as described herein.

Having now generally described the invention, the same will be more readily understood through reference to the following examples which are provided by way of illustration and are not intended to be limiting of the invention. The full text of references and published materials cited herein are incorporated by reference as if set forth at length.

EXAMPLES

Example 1

CD8:IGF1R Transgene Construct

The MMTV-CD8:IGF1R (MCI) construct shown in FIG. 2 and SEQ ID NO:1 was generated using standard molecular biology techniques, for example, Ausubel, F. M. et al., *Current Protocols in Molecular Biology*, John Wiley and Sons, Volume 2 (1991). A HindIII/BamHI fragment comprising the nucleotide sequence of SEQ ID NO:2 and encoding amino acid residues 1-218 of the human CD8 gene (SEQ ID NO:3) was cloned into the HindIII/BamHI site of pcDNA3.1(+) (Invitrogen™ Corporation, Carlsbad, Calif.). The full length human cDNA for IGF1R was obtained from R. Baserga (Thomas Jefferson University, Philadelphia, Pa.), Morrione et al., *J. Virology*, 69:5300-5303 (1995). The cytoplasmic catalytic domain was obtained using standard restriction enzyme techniques and subsequently, as a BamHI fragment of the IGF1R comprising the nucleotide sequence of SEQ ID NO:4 and encoding the amino acid sequence of SEQ ID NO:5, was inserted into at this site of the vector containing the CD8 fragment. Orientation and integrity of the CD8:IGF1R fusion sequence comprising the nucleotide sequence of SEQ ID NO:6 and encoding the amino acid sequence of SEQ ID NO:7 was detected by restriction analysis and confirmed by sequencing. To generate the transgene construct, the CD8:IGF1R fusion gene was then subcloned into the MMTV vector described by Mueller et al., *Cell*: 54, 105-115 (1988), resulting in the construct of FIG. 2 and SEQ ID NO:1. Orientation and integrity of the construct was confirmed by sequencing.

Example 2

Generation and Breeding of Transgenic Mice

Transgenic mice harboring the MMTV-CD8:IGF1R construct (MCI) were generated by microinjection of a PVUII fragment from the above construct into the pronucleus of C57B1/6XDBA2 F2 (B6D2F2) embryos. Embryos were generated by in-house mating of hybrid stud B6D2 males to virgin females from the same background (Harlan Sprague Dawley, Indianapolis, Ind.) using the techniques described by Hogan et al., *Manipulating the Mouse Embryo: a Laboratory Manual*, second edition, Brigid Hogan, Rosa Beddington, Frank Constantini, and Elizabeth Lacey, eds, Cold Spring Harbor Laboratory Press (1994). Injected embryos were transferred to pseudopregnant ICR female mice (Harlan Sprague Dawley, Indianapolis, Ind.) and allowed to develop to term. At five to eight days of age, toe and tail samples were taken for DNA analysis of the transgene. Mice harboring the transgene were identified by a polymerase chain reaction (PCR) strategy designed to detect the CD8:IGF1R fusion by using the oligos 5'AGGGTGTGGT-GAAAGATGAAC3' (SEQ ID NO:8) for the CD8 portion of the fusion, and 5'CGTCCGAGTAAGTGGTGAAGA3' (SEQ ID NO:9) for the IGF1R portion of the fusion. Founder mice (F0) shown to harbor the transgene were then outbred to the ICR background, and progeny (F1) were again tested for transmission of the transgene in a Mendelian fashion. Mice were observed twice daily for the presence of tumors in either the salivary gland or mammary gland, and the date of first observation of lesions was noted. Animals were euthanized when the tumors grew to about 1000 mg, or when the lesions impaired movement or feeding. All mice were housed in shoebox housing with food and water ad lib on a 12/12 light dark cycle, and were humanely handled under the guidelines of the institutional ACUC in an AAA-LAC accredited facility.

Example 3

Gene Expression Analysis

Detection of CD8:IGF1R transgene expression was performed by Northern blot analysis. To identify transgenic lines that had expression of the transgene, F1 offspring from founders were euthanized and their salivary glands were harvested. In addition, expression was analyzed in tumors from two lines of mice, as well as xenograft and cell line samples. For tissues, the samples were flash frozen in liquid nitrogen and stored until the time of mRNA isolation. Total RNA was isolated using a monophasic solution of phenol and guanidine isothiocyanates, such as the Trizol® LS Reagent system as described by the manufacturer (GIBCO™ Invitrogen Corporation, Carlsbad, Calif.). From these RNA isolates, mRNA was extracted using the Oligotex Direct mRNA kit as recommended by the manufacturer (Operon/QIAGEN, Valencia, Calif.). For cell lines, cells were lysed directly into the Trizol® lysis buffer, and stored at −80° C. until needed. The mRNA was resolved in 1.0% agarose gel electrophorsis under denaturing conditions with 17.6% formaldehyde and transferred to nylon membrane (Hybond-N, Amersham Biosciences, Uppsala, Sweden) by capillary blotting before hybridization. CD8:IGF1R messages were detected by hybridizing the RNA to a radiolabelled probe (Ready-to-Go kit, New England Nuclear/Perkin Elmer™ Life Sciences, Boston, Mass.) derived from the 3' end of the construct encoding the IGF1R tyrosine kinase domain. Hybridization was done in Rapid-hyb buffer (Amersham Biosciences, Uppsala, Sweden) overnight and nonspecific annealing of the probe was eliminated by multiple washes under stringent conditions (2×20 min in 0.1×SSC, 2% SDS at 65° C.). Specific hybridization of the probe to the CD8:IGF1R message was detected by exposing the blot to film (X-OMAT, Kodak Company, Rochester, N.Y.) overnight.

Example 4

Kinase Activity Analysis

To ensure that the message expressed from the transgene construct generated a constructively active IGF1R kinase domain, protein from several sources was analyzed for IGF1R specific activity. Samples analyzed were from the same tissues as described for the Northern Blot analysis. Tissues were homogenized in a Triton, Tris, and glycerol (TTG) lysis buffer (1% Triton X-100, 5% glycerol, 0.15M NaCl, 20 mM Tris-HCl, pH 7.6, 1 mM EDTA, 40 μM sodium vanadate, 40 μM ammonium molybdate) at 4° C. Proteins were quantitated using the micro BCA assay; 3 mg of total tissue lysate or IGF1R-Sal cells were immunoprecipitated with antibodies to CD8 (lanes c, d, f, g, h, i and j of FIGS. 4 and 7) or with antibodies to the IGF-1 receptor (lanes a, b and e of FIGS. 4 and 7). Proteins were separated on a 10% polyacrylamide gel and subjected to Western blot analysis using an anti-phosphotyrosine antibody (anti-pTyr). The filter was subsequently stripped and re-probed with an antibody to the IGF-1 receptor (anti-IGF1R) to insure equal protein loading.

Example 5

Establishment of Xenografts and Cell Lines

The establishment of xenografts and cell lines derived from said xenografts were carried out using protocols known to those skilled in the art, such as those described in Berger et al., Immunodeficient Mice in Oncology, *Contrib. Oncol. Basel,* Fiebig, H. H. and Berger, D. P. (eds), Vol. 42, 321-351, Karger (1992). Each nude mouse was given a subcutaneous implant of a tumor fragment (approximately 20 mg) obtained from a donor transgenic MCI-19 mouse bearing a spontaneously arising tumor. Implantation was accomplished using a 13-gauge trocar inserted subcutaneously in to the ventral side of the mouse, near the mammary gland. Nude (nu/nu) mice were obtained from Harlan Sprague Dawley Co. (Indianapolis, Ind.), and maintained in an ammonia-free environment in a defined and pathogen-free colony. Tumor growth was determined by measurement of tumors with a caliper once or twice a week until the tumors reached a predetermined "target" size of 1 gm. Tumor weights (mg) were estimated using the formula: tumor weight=(length×width$^2$)÷2. Xenograft IGF1R-Sal (MCI19 xenograft tumors) tumors grown in nude mice were excised and minced with scissors, and were dissociated using an enzyme cocktail consisting of 0.025% collagenase (Sigma Chemical Co., St Louis, Mo.), 0.05% pronase (Calbiochem, LaJolla, Calif.) and 0.04% DNase (Sigma) for 1 hour at 37° C. After removal of debris, by passing the cell suspensions through 70 μm nylon screens, the cells were washed in phosphate buffered saline (PBS), counted, and resuspended in complete RPMI™ (GIBCO™ Invitrogen Corporation, Carlsbad, Calif.) 1640 media supplemented with 10% heat inactivated fetal bovine serum (GIBCO™ Invitrogen Corporation, Carlsbad, Calif.). Cells (3×10E+5) were then seeded onto a variety of Biocoat Cellware® (Becton Dickinson, Franklin Lakes, N.J.) coated separately with the following extracellular matrix: collagen I, Laminin, fibronectin, Collagen IV, Poly-D-Lysine.

Example 6

Generation of Transgenic Mice with CD8:Her2 Transgene

Using the same approach as described in the Examples above, animals were also generated that contained a transgene encoding a fusion of the human CD8 transmembrane and extracellular domains to the intracellular kinase domains of the Her2/erbB2 gene (fusion sequence comprising the nucleotide sequence of SEQ ID NO:10 and encoding an amino acid of SEQ ID NO:11) (Plasmids 57584 and 59296 were obtained from ATCC and joined to make the full length clone of human Her2 (GenBank No. M11730); then used to form the fusion construct with human CD8). In a similar manner to the CD8:IGF1R transgene, the CD8:Her2 fusion protein is expressed under the control of the MMTV promoter. Thus, the construct was identical to that for the CD8:IGF1R transgene, except for the difference in the intracellular kinase domain. The construct was generated using molecular biology techniques known to those of skill in the art where a fragment comprising the nucleotide sequence of SEQ ID NO:12 encoding amino acids 1-218 of the CD8 gene (SEQ ID NO:13) were cloned in frame to a fragment comprising the nucleotide sequence of SEQ ID NO:14 encoding the C-terminal 570 amino acid Her2 kinase domain of SEQ ID NO:15 via an XhoI site and a connector (SEQ ID NO:16). The final construct, where the transcriptional fusion of the recombinant protein was cloned downstream of the MMTV promoter, was handled as described herein for the generation of mice for CD8:IGF1R. The CD8:Her2 mice (Her2 mice) developed mammary gland and salivary gland tumors, similar to the CD8:IGF1R mice and those generated by mutation to the rat neu gene (Mueller et al., Single-step induction of mammary adenocarcinoma in transgenic mice bearing the activated c-neu oncogene, *Cell*: 54, 105-115 (1988)). As with the CD8:IGF1R mice (MCI-15 And MCI-19), mammary gland and salivary gland tumors were established in xenografts and in cell culture for testing kinase inhibitors for specificity against the constructively activated Her2 tyrosine kinase receptor.

Example 7

Generation of Transgenic Mice with CD8:Met Transgene

Using the same approach as described in the Examples above, animals were also generated that contained a transgene encoding a fusion of the CD8 transmembrane and extracellular domains to the intracellular kinase domains of the cMet gene (fusion sequence comprising the nucleotide sequence of SEQ ID NO:17 encoding an amino acid of SEQ ID NO:18). In a similar manner to the CD8:IFG1R transgene, the CD8:Met fusion protein is expressed under the control of the MMTV promoter. Thus, the construct was identical to that for the CD8:IGF1R transgene, except for the difference in the intracellular kinase domain. The construct was generated using molecular biology techniques known to those of skill in the art where a fragment comprising the nucleotide sequence of SEQ ID NO:19 and encoding amino acids 1-218 of the CD8 gene (SEQ ID NO:20) were cloned in frame to a fragment comprising the nucleotide sequence of SEQ ID NO: 21 encoding the C-terminal 425 amino acid cMet kinase domain of SEQ ID NO:22 via a BamHI site and a connector (SEQ ID NO:23) (the human Met construct was obtained courtesy of G. Van der Woude, *P.N.A.S. U.S.A.*, 84:6379-6383 (1987)). The final construct, where the transcriptional fusion of the recombinant protein was cloned downstream of the MMTV promoter, was handled as described herein for the generation of mice for CD8:IGF1R. The CD8:Met mice (MCM mice, for Mmtv/Cd8/Met) developed mammary gland and salivary gland tumors, similar to the CD8:IGF1R mice described herein. As with the CD8: IGF1R mice (MCI-15 and MCI19), mammary gland and salivary gland tumors were established in xenografts as well as in cell culture for testing kinase inhibitors for specificity against the constructively activated cMet tyrosine kinase receptor.

Example 8

Evaluation of IGF1R Inhibitors

The proliferative activity of two IGF1R inhibitors in cells was evaluated in vitro against a cell line derived from a xenograft tumor generated in a transgenic mouse, IGF1R Sal (CD8-IGF1R), which was engineered to overexpress the catalytic domain of the human IGF1R. The two IGF1R inhibitors evaluated were a benzimidazole compound as described in WO02/079192 and U.S. application Ser. No. 10/263,448, hereby incorporated by reference, and paclitaxel. Inhibition of cellular proliferation was also determined in a variety of human tumor xenograft cell lines including, Colo205 (colon), Geo (colon), RD1 (rhabdomyosarcoma), H3396 (breast), and MDA PCa2b (prostate). Proliferation was evaluated by incorporation of [$^3$H]-thymidine into DNA after a 72 hour exposure to reagents. Cells were plated at 1,500 cells/well in 96-well microtiter plates and 24 hours later cells were exposed to a range of drug concentrations. After 72 hours incubation at 37° C., cells were pulsed with 4 µCi/ml [6-$^3$H] thymidine (Amersham Pharmacia Biotech, UK) for 3 hours, trypsinized, harvested onto UniFilter-96, GF/B plates (PerkinElmer, Boston, Mass.), and scintillation was measured on a TopCount.NXT (Packard, Conn.). Results are expressed as an $IC_{50}$, which is the drug concentration required to inhibit cell proliferation by 50% to that of untreated control cells. The $IC_{50}$ values for the compounds evaluated in this assay are shown in Table I.

TABLE I

| Compound | Cytotoxicity Assay $IC_{50}$ (nM) against IGF1R Sal tumor cell line[1] |
| --- | --- |
| benzimidazole compound | 120 |
| paclitaxel | 2.9 |

[1]Inhibition of proliferation was determined after a 72 h exposure by [$^3$H]-thymidine incorporation.

What is claimed is:

1. A transgenic mouse whose somatic and germ line cells comprise a genome comprised of a transgene encoding a constitutively activated tyrosine kinase receptor, said constitutively activated tyrosine kinase receptor comprising (a) the extracellular and transmembrane domains of CD8 and (b) the kinase domain of a kinase receptor selected from the group consisting of HER2, insulin-like growth factor I receptor (IGF1R), and hepatocyte growth factor receptor (Met), wherein the transgene is operably linked to a mouse mammary tumor virus (MMTV) promoter, and wherein the transgenic mouse exhibits mammary gland and salivary gland tumors that express said constitutively activated tyrosine kinase receptor.

2. The transgenic mouse of claim 1 wherein the kinase receptor is insulin-like growth factor I receptor (IGF1R).

3. The transgenic mouse of claim 1 wherein said constitutively activated tyrosine kinase receptor comprises the amino acid sequence of SEQ ID NO:7.

4. The transgenic mouse of claim 3 wherein said amino acid sequence is encoded by a nucleotide sequence comprising SEQ ID NO:6.

5. The transgenic mouse of claim 1 wherein said transgene comprises the nucleotide sequence of SEQ ID NO: 1.

6. The transgenic mouse of claim 1 wherein said constitutively activated tyrosine kinase receptor comprises the amino acid sequence of SEQ ID NO:11.

7. The transgenic mouse of claim 6 wherein said amino acid sequence is encoded by a nucleotide sequence comprising SEQ ID NO: 10.

8. The transgenic mouse of claim 1 wherein said constitutively activated tyrosine kinase receptor comprises the amino acid sequence of SEQ ID NO:18.

9. The transgenic mouse of claim 8 wherein said amino acid sequence is encoded by a nucleotide sequence comprising SEQ ID NO: 17.

10. The transgenic mouse of claim 1 wherein the kinase receptor is HER2.

11. The transgenic mouse of claim 1 wherein the kinase receptor is hepatocyte growth factor receptor (Met).

* * * * *